US012697222B2

(12) United States Patent
Jurick et al.

(10) Patent No.: US 12,697,222 B2
(45) Date of Patent: Aug. 4, 2026

(54) IMPLANTS WITH GROOVE PATTERNS AND SOFT TISSUE ATTACHMENT FEATURES

(71) Applicant: SMed-TA/TD, LLC, Columbia City, IN (US)

(72) Inventors: Joseph W. Jurick, Fort Wayne, IN (US); Paul S. Nebosky, Fort Wayne, IN (US); Gregory C. Stalcup, Fort Wayne, IN (US); Sarah L. Zimmerman, Mason, MI (US)

(73) Assignee: SMed-TA/TD, LLC, Columbia City, IN (US)

( * ) Notice: Subject to any disclaimer, the term of this patent is extended or adjusted under 35 U.S.C. 154(b) by 496 days.

(21) Appl. No.: 18/481,726

(22) Filed: Oct. 5, 2023

(65) Prior Publication Data

US 2024/0033094 A1    Feb. 1, 2024

Related U.S. Application Data

(60) Division of application No. 16/890,620, filed on Jun. 2, 2020, now abandoned, which is a division of
(Continued)

(51) Int. Cl.
*A61F 2/08* (2006.01)
*A61F 2/30* (2006.01)
(Continued)

(52) U.S. Cl.
CPC ........ *A61F 2/30771* (2013.01); *A61F 2/0811* (2013.01); *A61F 2/30767* (2013.01);
(Continued)

(58) Field of Classification Search
CPC ...... A61F 2/0811; A61F 2/3607; A61F 2/367; A61F 2002/0829; A61F 2002/0835; A61F 2002/0858; A61F 2002/0864
See application file for complete search history.

(56) References Cited

U.S. PATENT DOCUMENTS 3,977,026 A    8/1976    Battault
4,778,473 A    10/1988    Matthews et al.
(Continued)

FOREIGN PATENT DOCUMENTS

DE    10 2012 105 070 A1    12/2013
FR    2986962    8/2013

OTHER PUBLICATIONS

International Search Report dated Feb. 18, 2016 for International Application No. PCT/US2015/059528 (3 pages).
(Continued)

*Primary Examiner* — Brian A Dukert
(74) *Attorney, Agent, or Firm* — TAYLOR & EDELSTEIN, PC

(57) ABSTRACT

An orthopaedic implant includes: an implant body including a biocompatible material and configured to be implanted at an anatomical location, the implant body defining an attachment region on an outer surface of the implant body; an adjustable holder attached to the implant body and having a compression surface facing the attachment region, the adjustable holder being configured to be implanted at the anatomical location with the implant body and adjustably compress a soft tissue and/or a graft material between the compression surface and the attachment region; and a ratcheting mechanism attached to the implant body and configured to apply tension to the soft tissue and/or the graft material connected to the ratcheting mechanism.

18 Claims, 22 Drawing Sheets

Related U.S. Application Data application No. 15/586,642, filed on May 4, 2017, now Pat. No. 10,716,674, which is a continuation of application No. PCT/US2015/059528, filed on Nov. 6, 2015.

(60) Provisional application No. 62/076,901, filed on Nov. 7, 2014.

(51) Int. Cl.

| | | |
|---|---|---|
| *A61F 2/34* | (2006.01) | |
| *A61F 2/36* | (2006.01) | |
| *A61F 2/38* | (2006.01) | |

(52) U.S. Cl.

CPC ............. *A61F 2/34* (2013.01); *A61F 2/3607* (2013.01); *A61F 2/3662* (2013.01); *A61F 2/367* (2013.01); *A61F 2/3859* (2013.01); *A61F 2002/0829* (2013.01); *A61F 2002/0835* (2013.01); *A61F 2002/0858* (2013.01); *A61F 2002/0864* (2013.01); *A61F 2002/0888* (2013.01); *A61F 2002/30011* (2013.01); *A61F 2002/30537* (2013.01); *A61F 2002/30769* (2013.01); *A61F 2002/30827* (2013.01); *A61F 2002/30828* (2013.01); *A61F 2002/3083* (2013.01); *A61F 2002/30878* (2013.01); *A61F 2002/30904* (2013.01); *A61F 2002/3092* (2013.01); *A61F 2002/3093* (2013.01); *A61F 2002/30973* (2013.01); *A61F 2002/3403* (2013.01)

(56) References Cited

U.S. PATENT DOCUMENTS

| | | | |
|---|---|---|---|
| 4,778,474 | A | 10/1988 | Homsy |
| 4,944,759 | A | 7/1990 | Mallory et al. |
| 5,201,769 | A | 4/1993 | Schutzer |
| 5,314,488 | A | 5/1994 | Hayashi et al. |
| 5,370,698 | A | 12/1994 | Heimke et al. |
| 5,480,448 | A | 1/1996 | Mikhai |
| 5,702,397 | A | 12/1997 | Goble et al. |
| 5,972,032 | A | 10/1999 | Lopez et al. |
| 5,997,579 | A | 12/1999 | Albrektsson et al. |
| 6,152,961 | A | 11/2000 | Ostiguy, Jr. et al. |
| 6,231,612 | B1 | 5/2001 | Balay et al. |
| 6,290,726 | B1 | 9/2001 | Pope et al. |
| 6,290,727 | B1 | 9/2001 | Otto et al. |
| 6,626,949 | B1 | 9/2003 | Townley |
| 6,645,251 | B2 | 11/2003 | Salehi et al. |
| 6,908,486 | B2 | 6/2005 | Lewallen |
| 6,966,932 | B1 | 11/2005 | Schroeder |
| 7,553,332 | B2 | 6/2009 | Bacon |
| 7,597,715 | B2 | 10/2009 | Brown et al. |
| 7,641,698 | B1 | 1/2010 | Gibbs et al. |
| 7,833,274 | B2 | 11/2010 | Popoola et al. |
| 7,993,566 | B2 | 8/2011 | Pedersen et al. |
| 8,025,841 | B2 | 9/2011 | Lambert et al. |
| 8,088,169 | B2 | 1/2012 | Dorr et al. |
| 8,100,984 | B2 | 1/2012 | Lambert et al. |
| 8,350,186 | B2 | 1/2013 | Jones et al. |
| 8,444,699 | B2 | 5/2013 | Metzger et al. |
| 8,506,569 | B2 | 8/2013 | Keefer et al. |
| 8,556,986 | B2 | 10/2013 | Haidukewych |
| 8,821,582 | B1 | 9/2014 | Lyren |
| 8,834,576 | B1 | 9/2014 | Serafin, Jr. |
| 8,858,645 | B2 | 10/2014 | Grostefon et al. |
| 2004/0059427 | A1 | 3/2004 | Serbousek et al. |
| 2005/0102033 | A1 | 5/2005 | Lambert et al. |
| 2005/0171614 | A1 | 8/2005 | Bacon |
| 2006/0276906 | A1 | 12/2006 | Hoag et al. |
| 2010/0049329 | A1 | 2/2010 | Vio |
| 2010/0076572 | A1 | 3/2010 | Jamali |
| 2010/0114127 | A1 | 5/2010 | Lewallen |
| 2011/0009973 | A1 | 1/2011 | Meyers et al. |
| 2011/0015750 | A1 | 1/2011 | Popoola et al. |
| 2011/0123395 | A1 | 5/2011 | Lambert et al. |
| 2011/0130840 | A1 | 6/2011 | Oskouei |
| 2011/0213467 | A1 | 9/2011 | Lozier et al. |
| 2011/0218644 | A1 | 9/2011 | Meridew et al. |
| 2011/0270404 | A1 | 11/2011 | Khan et al. |
| 2013/0131741 | A1 | 5/2013 | Kourtis et al. |
| 2013/0184832 | A1 | 7/2013 | Haidukewych |
| 2013/0204389 | A1 | 8/2013 | Kumar et al. |
| 2013/0231750 | A1 | 9/2013 | Taylor |
| 2013/0324931 | A1 | 12/2013 | Meridew et al. |
| 2013/0338786 | A1 | 12/2013 | Haidukewych |
| 2013/0345822 | A1 | 12/2013 | Grostefon et al. |
| 2014/0012391 | A1 | 1/2014 | Gugler et al. |
| 2014/0172115 | A1 | 6/2014 | Porter et al. |

OTHER PUBLICATIONS

Extended European Search Report dated May 16, 2018 for European Application No. 17210893.8 (9 pages).
Supplementary Extended European Search Report dated Jul. 16, 2018 for European Patent Application No. 15 85 7897 (7 pages).

1606

1608

1610

1614

1612

1600

1604

1602

1616

1622

1618

IMPLANTS WITH GROOVE PATTERNS AND SOFT TISSUE ATTACHMENT FEATURES

CROSS REFERENCE TO RELATED APPLICATIONS

This is a division of U.S. patent application Ser. No. 16/890,620, entitled "IMPLANTS WITH GROOVE PATTERNS AND SOFT TISSUE ATTACHMENT FEATURES", filed Jun. 2, 2020, which is incorporated herein by reference. U.S. patent application Ser. No. 16/890,620 is a division of U.S. patent application Ser. No. 15/586,642, entitled "IMPLANTS WITH GROOVE PATTERNS AND SOFT TISSUE ATTACHMENT FEATURES", filed May 4, 2017, which issued as U.S. Pat. No. 10,716,674 on Jul. 21, 2020, and is incorporated herein by reference. U.S. patent application Ser. No. 15/586,642 is a continuation of PCT application No. PCT/US2015/059528, entitled "IMPLANTS WITH GROOVE PATTERNS AND SOFT TISSUE ATTACHMENT FEATURES", filed Nov. 6, 2015, which is incorporated herein by reference. PCT application No. PCT/US2015/059528 is based upon U.S. provisional patent application Ser. No. 62/076,901, entitled "IMPLANTS WITH GROOVE PATTERNS AND SOFT TISSUE ATTACHMENT FEATURES", filed Nov. 7, 2014, which is incorporated herein by reference.

BACKGROUND OF THE INVENTION

1. Field of the Invention

The present invention relates to orthopaedic implants.

2. Description of the Related Art

It is well-known to implant orthopaedic implants into a patient's body to attempt to restore musculoskeletal function that the patient has lost or damaged due to injury or disease. Many orthopaedic implants, for example, are meant to replace bone tissue that has failed to heal correctly or cannot be naturally repaired by the patient's body. Such known orthopaedic implants can include femoral knee implants, hip implants, glenoid implants, etc.

When implanting an orthopaedic implant, it is important that the orthopaedic implant is firmly anchored (fixated) in the body. Without being firmly fixated, there is a significant risk that the implant will loosen due to movement of the surrounding anatomy, leading to implant failure and potentially more damage to the surrounding anatomy of the patient. To fixate implants in the body, traditionally an adhesive compound, known as bone cement, was used in order to provide temporary fixation before the material of the implant was integrated in the body to permanently fixate the implant.

One known issue with bone cement is that the cement substance is difficult to work with during surgery. Bone cement has a consistency very similar to normal cement and putties, which makes the bone cement difficult to remove from areas where it is not desired. If the incorrectly placed bone cement is not adequately removed, the bone cement can damage the anatomy adjacent to the implant during normal movement. To lessen the risk of this occurring, a surgeon might opt to use less bone cement to temporarily fixate the implant, but lessening the amount of bone cement used presents the risk of not using enough bone cement and not properly fixating the implant.

An alternative to using bone cement is using a fixation device, such as a bone pin or screw, that connect the implant to surrounding bone tissue. Such fixation devices can be effective, but can require significantly more operation time and planning to correctly install. Further, such fixation devices must be fixated in adjacent bone tissue by forcing the fixation devices into the adjacent bone tissue, which can cause damage to the adjacent bone tissue that will need to be surgically repaired.

One approach that has been tried to remove the need for bone cement is to put a porous ingrowth material on the implant that encourages bone ingrowth into and bonding with the pores of the material. The filling of the pores with bone material that bonds with the implant is an attractive solution, but the time necessary for sufficient bone ingrowth into the pores is a significant period during which the patient is unable to move the area where the implant is fixated. In the event that the patient moves or the implant otherwise manages to move during the bone ingrowth phase, there is also a possibility that the bone material in the pores will shear from the surrounding bone tissue and the pores will be filled with bone material that provides no fixation. In light of such risks, most implants that have fixating ingrowth material will still utilize bone cement or another fixation method, such as bone screws, to sufficiently fixate the implant following implantation.

What is needed in the art is a way to fixate orthopaedic implants in a patient's body that overcomes some of the previously described disadvantages.

SUMMARY OF THE INVENTION

The present invention provides an implant with a porous ingrowth material having grooves formed in the ingrowth material.

The invention in one form is directed to an orthopaedic implant that includes: an implant body including a biocompatible material and configured to be implanted at an anatomical location, the implant body defining an attachment region on an outer surface of the implant body; an adjustable holder attached to the implant body and having a compression surface facing the attachment region, the adjustable holder being configured to be implanted at the anatomical location with the implant body and adjustably compress a soft tissue and/or a graft material between the compression surface and the attachment region; and a ratcheting mechanism attached to the implant body and configured to apply tension to the soft tissue and/or the graft material connected to the ratcheting mechanism.

The invention in another form is directed to a method of affixing a soft tissue and/or a graft material to an orthopaedic implant, the method including: implanting the orthopaedic implant at an anatomical location, the orthopaedic implant including: an implant body including a biocompatible material and defining an attachment region on an outer surface of the implant body; an adjustable holder attached to the implant body and having a compression surface facing the attachment region; and a ratcheting mechanism attached to the implant body; compressing the soft tissue and/or the graft material between the compression surface of the adjustable holder and the attachment region of the implant body; and wrapping the soft tissue and/or the graft material around the ratcheting mechanism.

An advantage of the present invention is the grooves formed in the porous ingrowth material can provide additional friction to keep the implant fixated while bone material grows into the pores to permanently fixate the implant.

Another advantage is the grooves can be adjusted in many different ways to suit the specific requirements of the implant.

Yet another advantage is the grooves can also aid tissue attachment to the implant.

Yet another advantage is the grooves can make the implant easy to install but difficult to remove.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

The present invention provides implants with grooved features that prevent implant movement, aid tissue attachment, make the implant easier to insert but more difficult to remove, or some combination of the aforementioned features. The present invention also relates to manufacturing methods for such implants.

Figure 1:
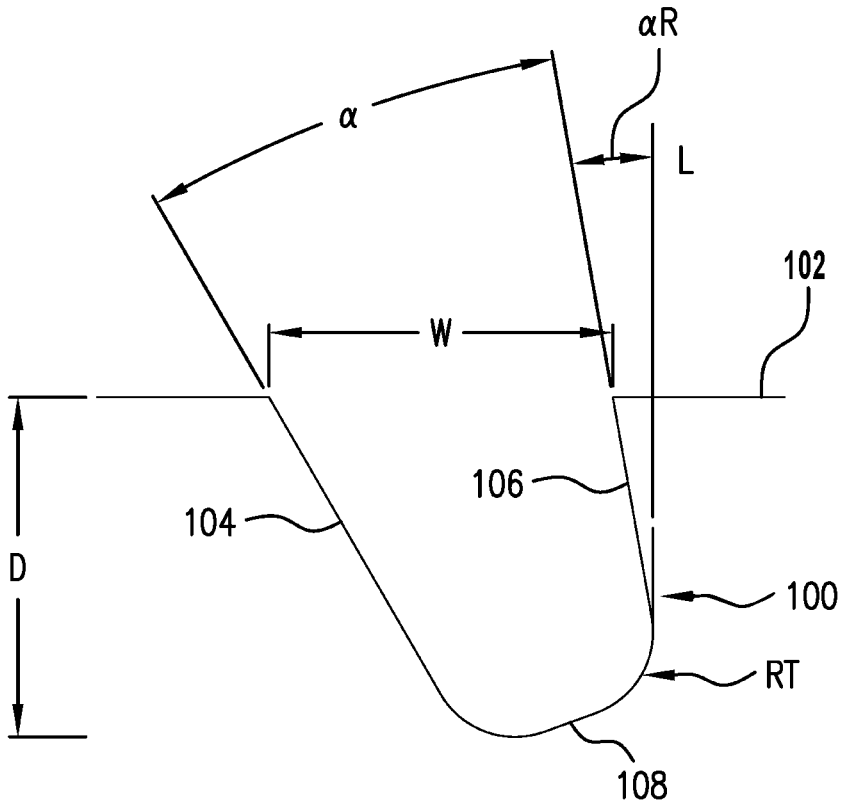
FIG. 1 is a side view of an embodiment of a single groove formed in a porous material according to the present invention.

Referring now to FIG. 1, an example groove 100 is shown that may be included on one or more surfaces 102 of an orthopedic implant. The groove 100 can be one of many grooves located on a porous section of the implant, a solid implant substrate, or a combination of the two. The grooves can have one or more of the following purposes: preventing motion, migration, back-out, tilting, translation, and rotation of the implant; aiding tissue attachment to the implant; and easing implant insertion at an implantation site while increasing the difficulty of implant removal. It should be appreciated that the previously described purposes are exemplary only and grooves can be added to medical implants according to the present invention for any desired purpose.

Grooves added to a medical implant can be varied between different medical implants or different regions of the same medical implant. Some of the ways in which the grooves can be varied include: the location of the grooves, the grooves' pattern(s), the orientation of the grooves, the distance between grooves, and individual groove geometry. As can be seen in FIG. 1, each groove 100 can be formed with a first groove wall 104 and a second groove wall 106 with the groove 100 defining a depth D from the surface 102 to a bottom 108 of the groove 100, a width W between the first groove wall 104 and second groove wall 106, a groove angle $\alpha$ defined between the first groove wall 104 and second groove wall 106, the bottom 108 defining a tip radius RT so the groove 100 has a curvature at the bottom 108, and the groove 100 can further define a rake angle $\alpha R$ relative to a normal line L of the surface 102, which is shown as a negative rake angle in FIG. 1. It should be appreciated that the depth D, width W, groove angle $\alpha$, tip radius RT, and rake angle $\alpha R$ can all be varied, as desired, to form differently shaped grooves in the surface 102. While the groove 100 shown in FIG. 1 is shown as being formed in the surface 102 by removing material from the surface 102, grooves can also be formed on the surface 102 by the addition of material to the surface 102, such that the surface 102 defines a bottom of the groove.

The groove 100 shown in FIG. 1 has a negative rake angle $\alpha R$ relative to the normal line L of the surface 102. Negative rake angles can help with motion prevention and be used to make hooks to aid soft tissue attachment. Likewise, combining negative rake angles with the proper groove location, pattern, and orientation can make the implant easier to implant but more difficult to remove, which is described further herein.

The grooves can be added to the solid regions of an implant, the porous regions of an implant, or both. The groove geometry, location, orientation, and pattern allow the implant to resist motion. In cases where grooves are added to the porous region of the implant, bone and tissue ingrowth into the grooves over time also can improve the motion resistance characteristics of the implant.

Grooves can be added to many different types of medical or orthopedic implants. Examples include, but are not limited to acetabular shells, femoral hip stems, femoral knee implants, tibial knee implants, patellar implants, shoulder implants, spine implants, small joint implants, hand implants, ankle implants, foot implants, large reconstruction implants, and dental implants.

The grooves can be manufactured onto implants using the following described methods or any other known methods. Example methods that can be used to manufacture the groove onto a medical implant can include forging, casting, photochemical etching, standard (also called RAM or plunge) electrical discharge machining (EDM), wire EDM, machining, laser etching, rolling, and grinding.

Figure 2:
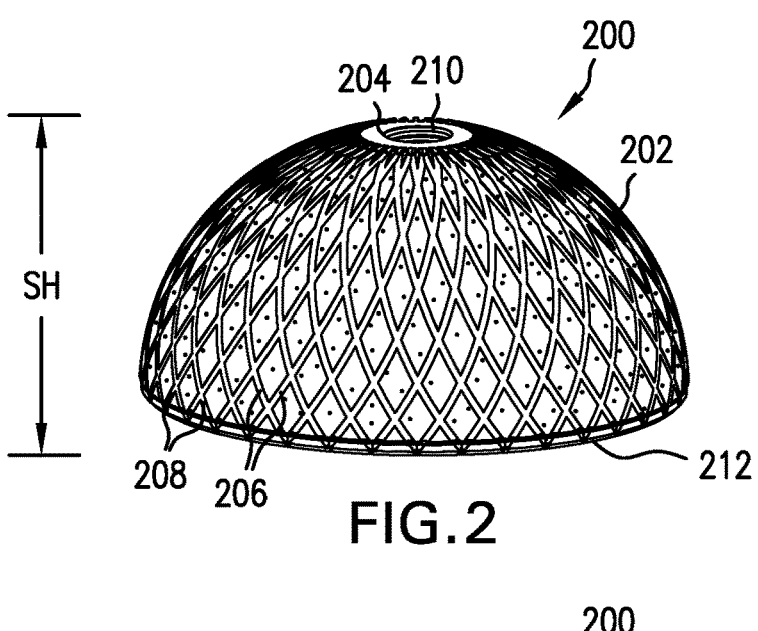
FIG. 2 is a perspective view of an embodiment of an acetabular cup according to the present invention with crossing helical grooves formed in a porous material.
Figure 3:
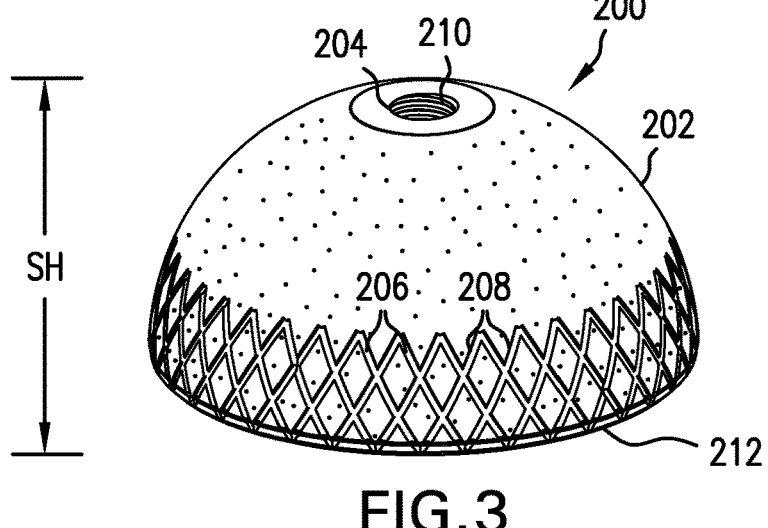
FIG. 3 is a perspective view of the acetabular cup shown in FIG. 2 with a different groove pattern.
Figure 4:
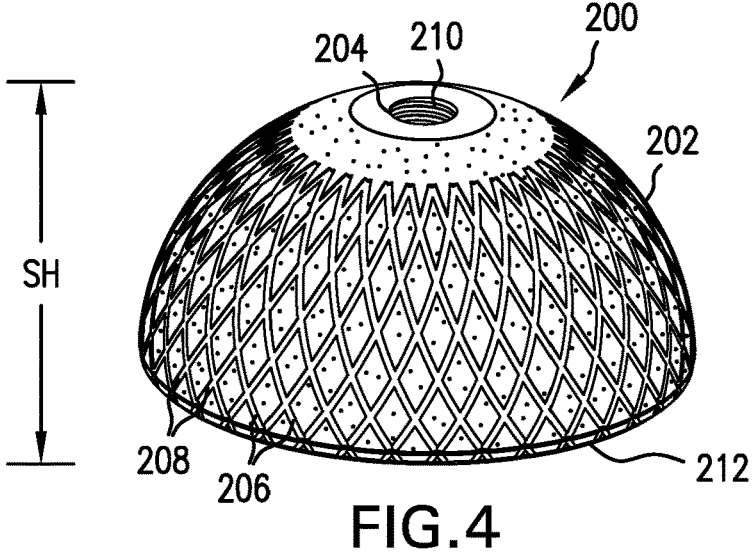
FIG. 4 is a perspective view of the acetabular cup shown in FIG. 2 with yet a different groove pattern.

Referring now to FIGS. 2-4, embodiments of an orthopaedic implant 200 according to the present invention are shown with differing groove patterns formed in a porous ingrowth material 202 posited on a semi-spherical shell 204, which can also be referred to as an implant body. Since the orthopaedic implant 200 is intended to be implanted in a patient, the implant body 204 should be formed of a biocompatible material that is suitable for implantation into the patient. Examples of such materials can be, but are not limited to, metals such as titanium, nitinol, stainless steel, cobalt-chrome, and tantalum, as well as various polymers such as polyaryl etherketones (PAEK), polyethylene, polylactic acid (PLA), etc. The porous ingrowth material 202, similarly, should be biocompatible and also allow for tissue infiltration into pores formed in the porous ingrowth material 202. The porous ingrowth material 202 can be, for example, a metal with pores formed into the metal, a polymer with pores formed into the polymer, a metal foam, a polymer foam, a ceramic foam, etc. It should be appreciated that the given examples are exemplary only and any biocompatible material that is porous can serve as the porous ingrowth material 202. To further assist tissue infiltration and integration into the porous ingrowth material 202, some or all of the pores formed in the porous ingrowth material 202 can contain various bioactive substances that serve various roles. The bioactive substances can be, for example, tissue growth factors, antibiotics, anti-inflammatories, and painkillers. The porous ingrowth material 202 can be posited on a surface of the implant body 204 so that the porous ingrowth material 202 is a discrete element of the orthopaedic implant 200 or the porous ingrowth material 202 can also be formed as a part of the implant body 204 so the exposed surface(s) of the porous ingrowth material 202 forms a part of the exposed surface(s) of the implant body 204. It can therefore be seen that the porous ingrowth material 202 can be provided as part of the orthopaedic implant 200 in many different configurations to provide a region of the orthopaedic implant 200 that encourages tissue ingrowth and fixation of the implant 200 in the patient.

As can be seen, helical grooves 206 with a first direction can be formed in the porous ingrowth material 202 that are crossed by helical grooves 208 with a second direction opposite to the first direction. This forms a pattern of crossing helical grooves 206, 208 in the porous ingrowth material 202. The purposes of these grooves 206, 208 are to prevent rotation and tilting of the shell 204 that can occur after the orthopaedic implant 200 is placed in a patient's anatomy. Groove coverage may be 0-100% of a shell height SH of the shell 204, which can be varied as shown in FIGS. 2-4, and the groove(s) 206, 208 may originate from an apex 210 of the shell 204, a bottom 212 of the shell 204, or any point in between. It should be appreciated that when referring to percentages of the "shell height" SH of the shell 204 that are covered by a groove, reference is being made to a single groove extending along a certain percentage of one height. For example, a single groove that extends from the apex 210 of the shell 204 to the bottom 212 of the shell 204 along the outer surface of the shell 204 would be considered as covering 100% of the shell height SH, as shown in FIG. 2, of the shell 204, whereas a groove that only extended halfway between the apex 210 of the shell 204 to the bottom 212 of the shell 204 along the outer surface of the shell 204 would be considered as covering 50% of the shell height SH. The location, pattern, orientation, and distance between the grooves 206, 208 can vary, as can be seen in FIGS. 2-4. In addition to the shell height SH of the grooves 206, 208 being adjusted, a spacing distance SD between similarly directed grooves 206, 208 can be altered to adjust the number of grooves 206, 208 formed in the porous ingrowth material 202. Likewise, the groove geometry of each formed groove, which can include the width W, depth D, groove angle $\alpha$, rake angle $\alpha R$, and tip radius RT as shown in FIG. 1, can be similar for all grooves or vary between the grooves, as desired. As shown in FIGS. 2-4, the grooves 206, 208 can have a cross pattern with helical angles ranging from 15° to 60°. Similarly directed grooves 206 and 208 can be located 5° to 45° from each other on the hemisphere. Further, the individual grooves can have a depth D of 0.005" to 0.040", a width W of 0.005" to 0.080", a tip radius RT of 0.001" to 0.040", and a groove angle $\alpha$ of 0° to 120°. Further, the rake angle $\alpha R$ for the grooves 206, 208 can be in a range from −60° to +60°.

The grooves 206, 208 can cover the entire shell height SH of the shell 204, or a portion of the shell 204 as shown. Helical groove coverage on the shell 204 can range from 0% to 100% of the shell height SH as well as 5 to 75% of a total surface area of the porous ingrowth material 202. The grooves 206, 208 may start at the apex 210 of the shell 204, bottom 212 of the shell 204, or any point in between, as shown.

Figure 5:
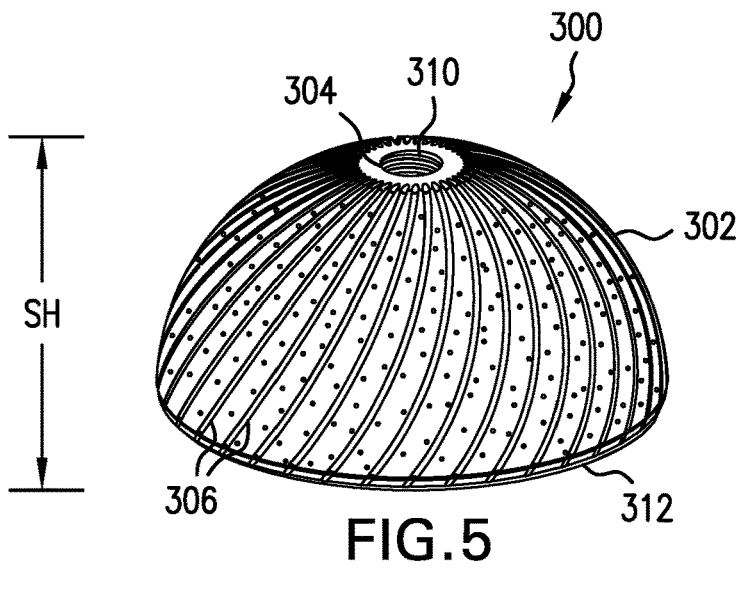
FIG. 5 is a perspective view of an embodiment of an acetabular cup according to the present invention with non-crossing helical grooves formed in a porous material.
Figure 6:
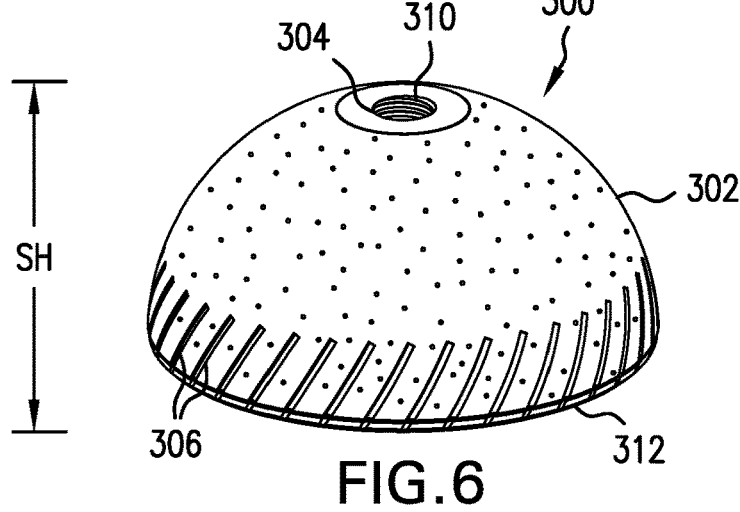
FIG. 6 is a perspective view of the acetabular cup shown in FIG. 5 with a different groove pattern.
Figure 7:
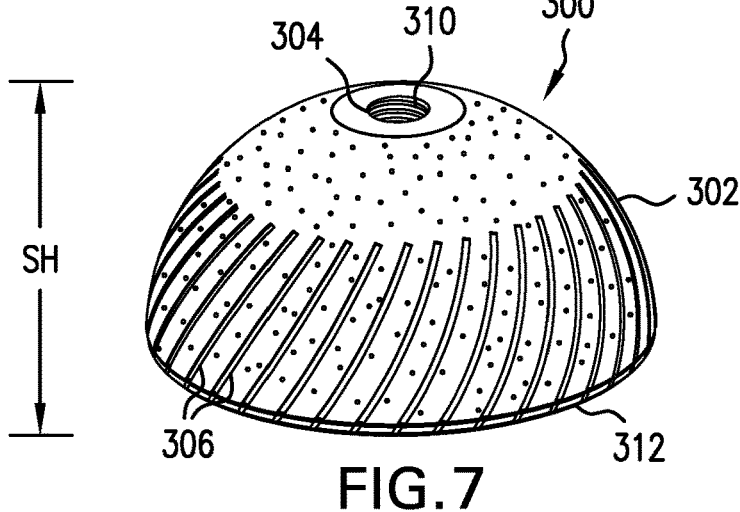
FIG. 7 is a perspective view of the acetabular cup shown in FIG. 5 with yet a different groove pattern.

Referring now to FIGS. 5-7, another embodiment of an orthopaedic implant 300 is shown that includes a porous ingrowth material 302 on a semi-spherical shell 304 that has grooves 306 formed therein. The orthopaedic implant 300 is similar to the orthopaedic implants 200 shown in FIGS. 2-4, with all similar elements being numbered similarly with values raised by 100. As can be seen, the grooves 306 are helical, similar to the grooves 206, 208 shown in FIGS. 2-4, but all the grooves 306 are similarly directed so that none of the grooves 306 cross another groove. Such a configuration of grooves 306 can help prevent rotation and tilting of the shell 304 following implantation. Groove coverage may be 0-100% of a shell height SH of the shell 304, and the grooves 306 may originate from the apex 310 of the shell 304, the bottom 312 of the shell 304, or any point in between. The location, pattern, orientation, and distance between the grooves 306 can vary. The grooves 306 can have a clockwise or counter-clockwise curvature.

Likewise, each individual groove 306 can have varying groove geometry, as previously described, with dimensions that can be varied similar to the previously described grooves 206 and 208. The grooves 306 can cover the entire shell height SH of the shell 304, as shown in FIG. 5, or a portion of the shell 304, as shown in FIGS. 6-7. Helical groove coverage on the shell 304 can range from 0% to 100% of the shell height SH and between 5 and 75% of the total surface area of the porous ingrowth material 302.

Figures 8, 9, 10:
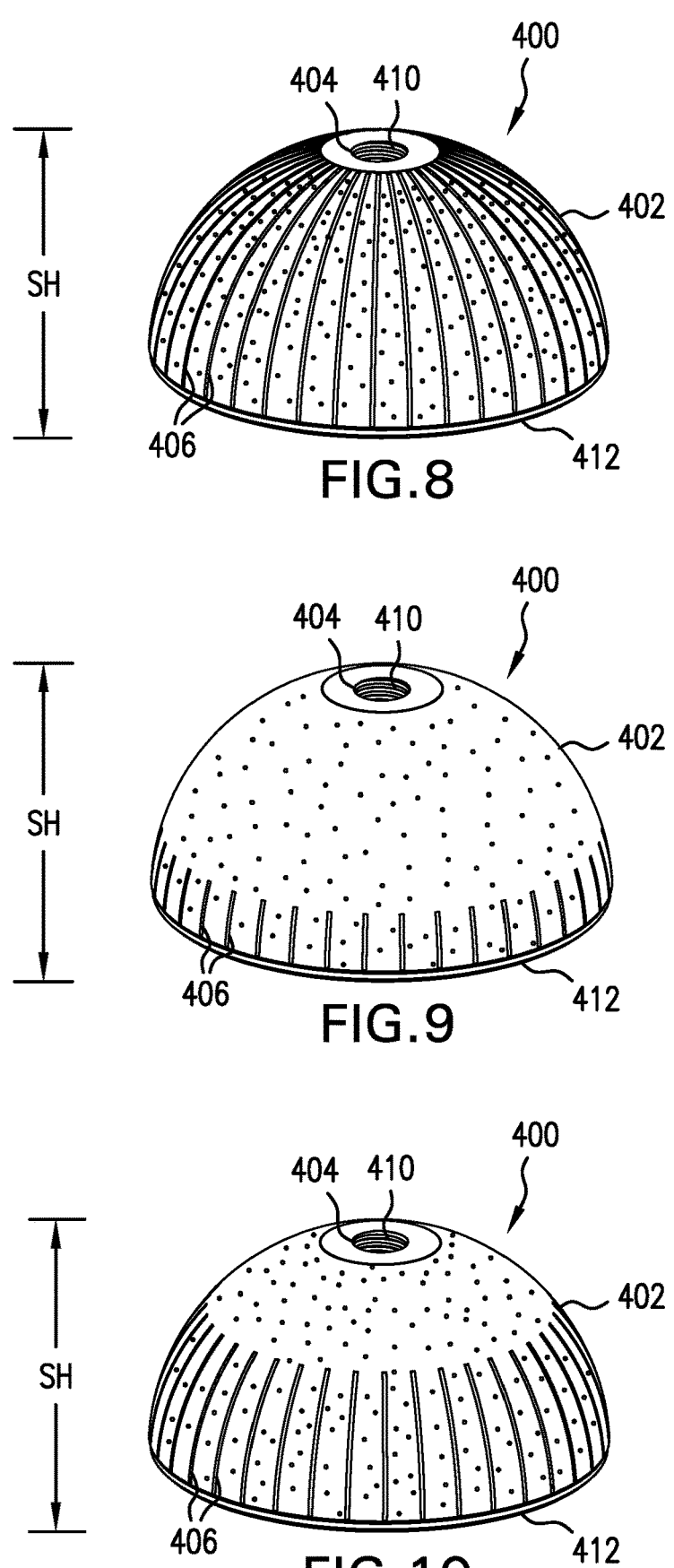
FIG. 8 is a perspective view of an embodiment of an acetabular cup according to the present invention with longitudinal grooves formed in a porous material.
FIG. 9 is a perspective view of the acetabular cup shown in FIG. 8 with a different groove pattern.
FIG. 10 is a perspective view of the acetabular cup shown in FIG. 8 with yet a different groove pattern.
Figure 11:
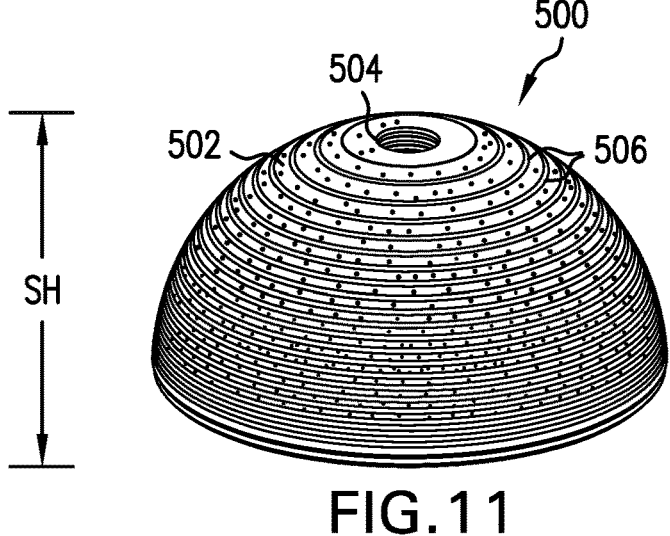
FIG. 11 a perspective view of an embodiment of an embodiment of an acetabular cup according to the present invention with latitudinal grooves formed in a porous material.
Figure 12:
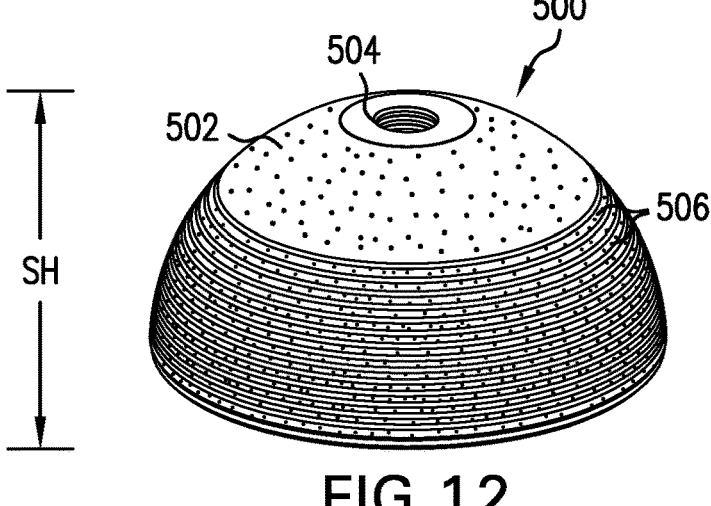
FIG. 12 is a perspective view of the acetabular cup shown in FIG. 11 with a different groove pattern.
Figure 13:
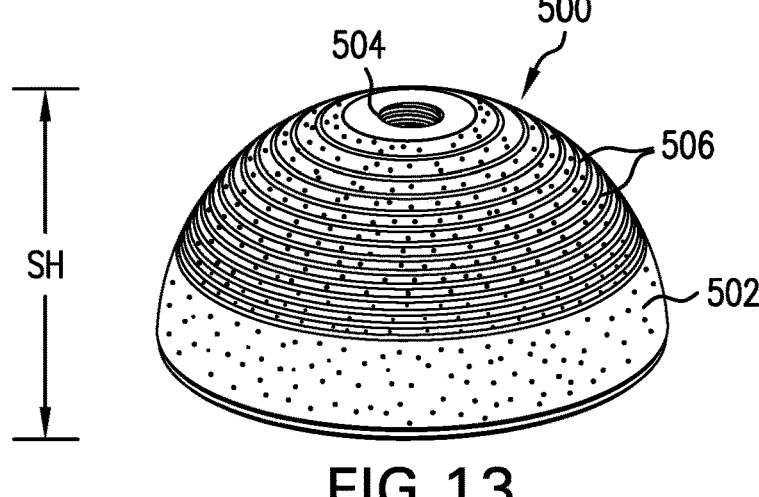
FIG. 13 a perspective view of the acetabular cup shown in FIG. 11 with yet a different groove pattern.
Figure 14:
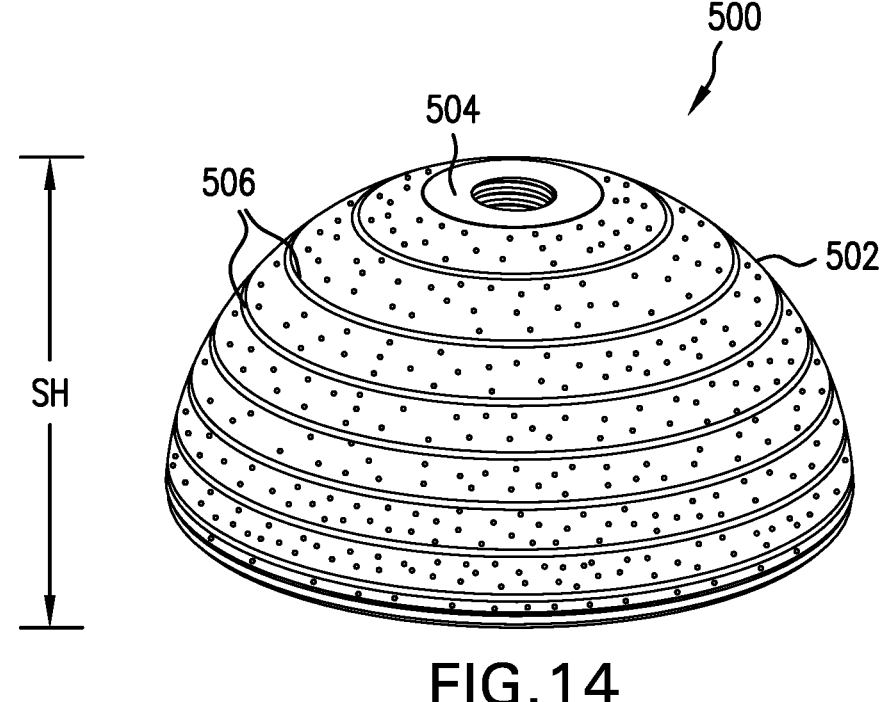
FIG. 14 a perspective view of the acetabular cup shown in FIG. 11 with yet a different groove pattern.

Referring now to FIGS. 8-10, another embodiment of an orthopaedic implant 400 according to the present invention is shown that includes a porous ingrowth material 402 on a semi-spherical shell 404 with longitudinal grooves 406 formed therein. The orthopaedic implant 400 is similar to the orthopaedic implants 200 shown in FIGS. 2-4, with all similar elements being numbered similarly with values raised by 200. The longitudinal grooves 406 can prevent rotation of the shell 404 following implantation. As used herein, "longitudinal" refers to the grooves 406 being formed in the porous ingrowth material 402 such that the grooves 406 form normal angles relative to the bottom 412 of the shell 404 and are not angled with respect to the bottom 412 like the previously described helical grooves 206, 208, 306. The grooves 406 can cover 0-100% of the shell height SH, and the grooves 406 may originate from the apex 410 of the shell 404, the bottom 412 of the shell 404, or any point in between. The location, pattern, orientation, and distance between the grooves 406 can vary. Likewise, the groove geometry of each groove 406 can be similar or vary, as previously described. One embodiment consists of longitudinal grooves that are located 5° to 45° from each other on the hemisphere. Further, the individual grooves 306 can have a depth D of 0.005" to 0.040", a width W of 0.005" to 0.080", a tip radius RT of 0.001" to 0.040", and a groove angle $\alpha$ of 0° to 120°. Further, the rake angle $\alpha R$ can range from −60° to +60°. The grooves 406 can cover anywhere from 5 to 75% of the total surface area of the porous ingrowth material 402. The spacing between adjacent grooves 406 can be altered to give varying number of grooves 406 in the porous ingrowth material 402.

Referring now to FIGS. 11-14, an embodiment of an orthopaedic implant 500 according to the present invention is shown that includes a porous ingrowth material 502 on a semi-spherical shell 504 with latitudinal grooves 506 formed in the porous ingrowth material 502. The orthopaedic implant 500 is similar to the orthopaedic implants 200 shown in FIGS. 2-4, with all similar elements being numbered similarly with values raised by 300. The latitudinal grooves 506 can help prevent tilting of the shell 504 following implantation in a patient. The latitudinal grooves 506 can be formed in the porous ingrowth material 502 such that the grooves 506 extend along multiple circumferences of the outer surface of the shell 504. In this sense, the grooves 506 can have differing lengths based on where the groove is formed on the outer surface. Alternatively, one or more of the grooves 506 can be formed to not extend across the entirety of a circumference, so that the groove(s) has distinct longitudinal ends rather than being a continuous groove formed in the circumference. The location, pattern, orientation, and distance between the grooves can vary, as shown in FIGS. 11-14. Likewise, the groove geometry of each individual groove 506 can be varied, as previously described. The latitudinal groove 506 can be located 0.010" to 0.500" from each other. Further, each groove can have a depth D of 0.005" to a width W of 0.005" to 0.080", a tip radius RT of 0.001" to 0.040", and a groove angle $\alpha$ of 0° to 120°. Further, the rake angle αR for one or more of the grooves 506 can range from −60° to +60°.

The grooves 506 can cover the entire shell height SH of the shell 504 or a portion of the shell 504 as shown. Groove coverage on a shell 504 can range from 0% to 100% of the shell height SH and the grooves 506 can encompass a total surface area of the porous ingrowth material 502 ranging between 5 and 75%.

Figures 15, 16:
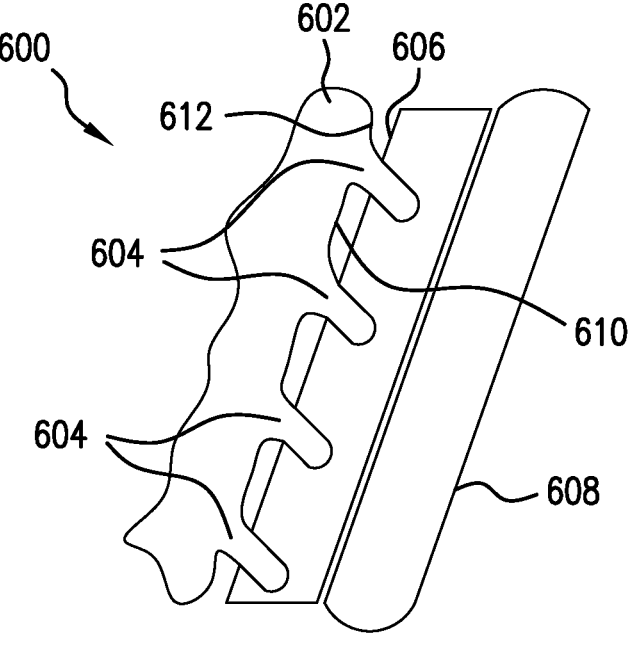
FIG. 15 is a side view of an embodiment of an orthopaedic implant according to the present invention that includes hooks formed in a porous material for holding soft tissue.
FIG. 16 is a side view of an embodiment of hooks that can be formed in the orthopaedic implant shown in FIG. 15.
Figure 17:
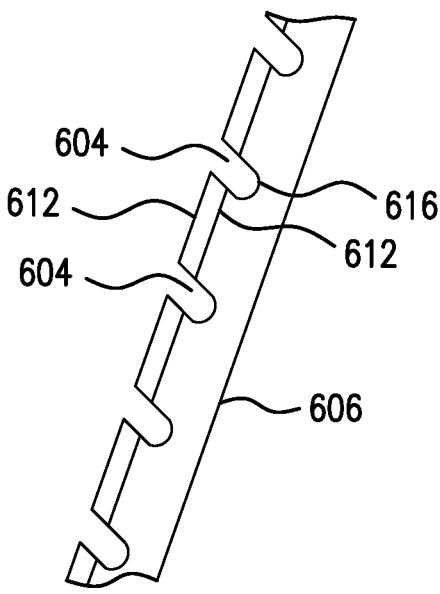
FIG. 17 is a side view of another embodiment of hooks that can be formed in the orthopaedic implant shown in FIG. 15.
Figure 18:
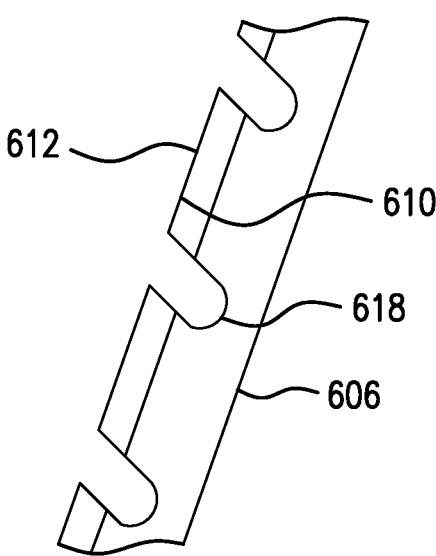
FIG. 18 is a side view of yet another embodiment of hooks that can be formed in the orthopaedic implant shown in FIG. 15.

Referring now to FIGS. 15-18, another embodiment of an orthopaedic implant 600 according to the present invention is shown that has an implant body 602 with a plurality of hooks 604 for attaching a graft 606 to the implant body 602 and a cover 608 attached to the implant body 602 that can protect the graft 606 from being impacted by surrounding anatomical features. The hooks 604 can be formed to have a negative rake angle to aid soft tissue or soft tissue graft attachment, as shown. The hooks 604 can be formed, for example, by forming grooves 610 into the implant body 602 such that the hooks 604 are formed between adjacent grooves 610. The hooks 604 can aid soft tissue attachment to the implant body 602 without killing the soft tissue due to excessive pressure and restriction of blood flow, with the cover 608 acting to protect the soft tissue or graft 606 from being forced against the hooks 604. The location, pattern, orientation, and distance between the grooves 606 can vary. Further, the groove geometry for the hooks 604 can be varied, as previously described and can be seen in comparing the hooks 604 shown in FIGS. 15-18. The cover 608 can also help keep the soft tissue in place until it grows into the grooves 610. The hooks 604 can, for example, be angled relative to a surface 612 of the implant body 602 with relatively small, round tips 614, as shown in FIG. 16; perpendicular relative to the surface 612 with relatively small, square tips 616, as shown in FIG. 17; or angled relative to the surface 612 with relatively large, round tips 618, as shown in FIG. 18. Since the grooves 610 are shaped to keep the soft tissue in place, the cover 608 can be applied with little to no compressive force on the soft tissue, preventing compressive force from constricting and killing the soft tissue. One example embodiment of the invention utilizing such a configuration can be a large oncology reconstructive femoral stem where a tendon of the patient is attached directly to the femoral stem.

Figure 19:
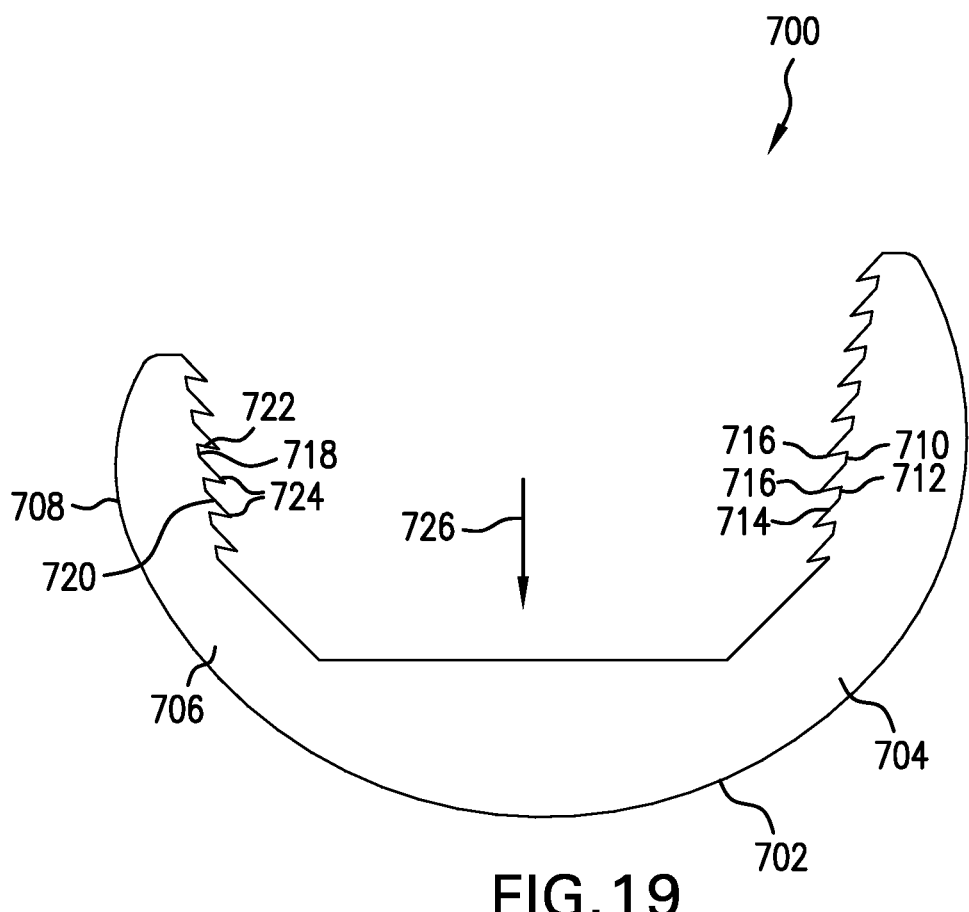
FIG. 19 is a side view of an embodiment of a femoral knee implant according to the present invention that has a porous material with grooves formed therein.

Referring now to FIG. 19, another embodiment of an orthopaedic implant 700 according to the present invention is shown that includes an implant body 702 formed as a femoral knee implant with a mounting portion 704 connected to at least one femoral head portion 706 with an outer articulating surface 708. The mounting portion 704 can rest on a femur while the femoral head portion 706 can be placed at an end of the femur so that the articulating surface 708 of the femoral head portion 706 can articulate with a tibia. To help with keeping the implant body 706 fixated to the femur, a porous ingrowth material 710 can be placed on an interior surface 712 of the mounting portion 704 and formed with grooves 714 to form a series of serrated hooks 716 in the porous ingrowth material 710. Further, an additional porous ingrowth material 718 can be attached to an interior surface 720 of the femoral head portion 706 that also has grooves 722 formed therein to form a series of serrated hooks 724 in the porous ingrowth material 718. The grooves 714 and 722 forming the hooks 716, 724 can inhibit implant 700 motion after implantation due to the shape of the hooks 716, 724 being such that the hooks 716, 724 all point in a similar vertical direction 726 to allow the tips of the hooks 716, 724 to easily slide along a bone surface as the knee implant 702 is placed on the femur while digging into the bone surface if the knee implant 702 is moved away from the femur. The location, pattern, orientation, and distance between the grooves 714, 722 can vary to form a desired pattern of hooks 716, 724. Further, the groove geometry of each groove 714, 722 can be varied as previously described. The grooves 714, 722 can be located 0.010″ to 0.500″ from adjacent grooves 714, 722 in the same porous ingrowth material 710, 718. Further, the grooves 714, 722 can have a depth D of 0.005″ to 0.040″, a width W of 0.005″ to 0.080″, a tip radius RT of 0.001″ to 0.040″, a groove angle α of 0° to 120°. Further, the rake angle αR of the grooves 714, 722 can range from −60° to +60°.

Figure 20:
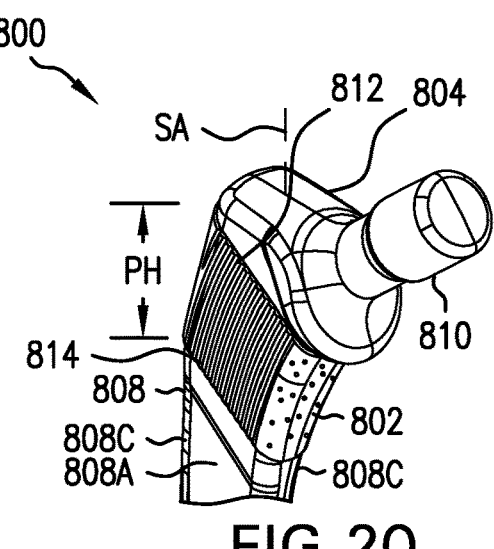
FIG. 20 is a perspective view of an embodiment of a femoral hip stem according to the present invention with a porous material having grooves formed therein.
Figure 21:
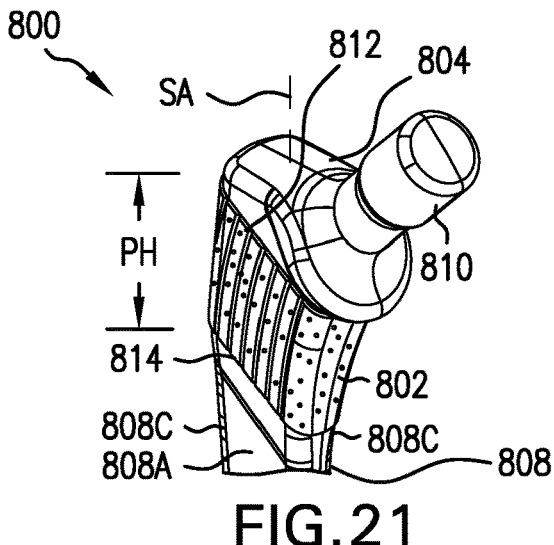
FIG. 21 is a perspective view of the femoral hip stem shown in FIG. 20 with a different groove pattern formed in the porous material.
Figure 22:
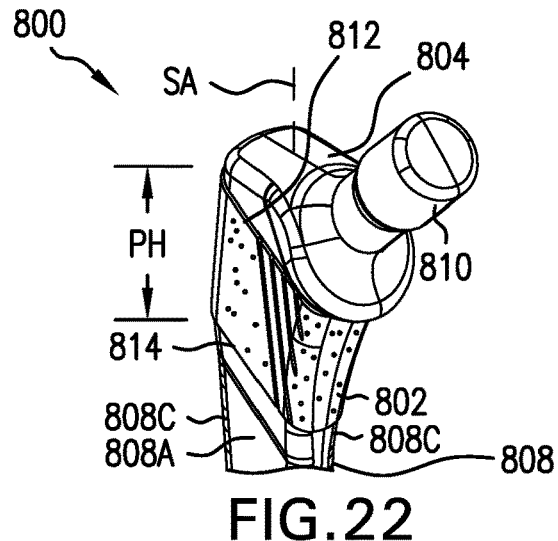
FIG. 22 is a perspective view of the femoral hip stem shown in FIG. 20 with yet another different groove pattern formed in the porous material.

Referring now to FIGS. 20-24, another embodiment of an orthopaedic implant 800 is shown that includes a porous ingrowth material 802 placed on an implant body 804, shown as a femoral hip stem, that has grooves 806 formed in the porous ingrowth material 802. The hip stem 804 defines a stem axis SA and includes a femoral portion 808 that will be implanted into a femur and an acetabular portion 810 connected to the femoral portion 808 that will be implanted in an acetabulum. The femoral portion 808 has an anterior face 808A, a posterior face 808B (shown in FIG. 24), and a pair of side faces 808C connected to the anterior face 808A and posterior face 808B. As shown, the porous ingrowth material 802 is placed on each face 808A, 808B, and 808C of the femoral portion 808 near the connection between the femoral portion 808 and the acetabular portion 810. The grooves 806 can be formed in the porous ingrowth material 802 on the anterior face 808A and/or the posterior face 808B and can help prevent movement of the hip stem 804 in the medial to lateral direction and ease implant insertion. The grooves 806 can be oriented generally along the stem axis SA (as shown in FIGS. 20-21), perpendicular to the stem axis SA, or angled relative to the stem axis SA (as shown in FIG. 22). The grooves 806 may be formed as continuous straight lines in the porous material 802 or curved. The grooves 806 may cover between 0 and 100% of a proximal porous material height PH, and the grooves 806 may originate from a proximal end 812 of the porous material 802, a distal end 814 of the porous material 802, or any point in between. The location, pattern, orientation, and distance between the grooves 806 can vary. Likewise, the groove geometry, can vary as previously described. One example embodiment consists of curved grooves located 0.010″ to 0.500″ from each other that travel from the proximal end 812 to the distal end 814 of the proximal porous material 802. The individual grooves can have a depth D of 0.005″ to 0.040″, a width W of 0.005″ to 0.080″, a tip radius RT of 0.001″ to 0.040″, a groove angle α of 0° to 120°. Further, the rake angle αR can range from −60° to +60°.

Figure 23:
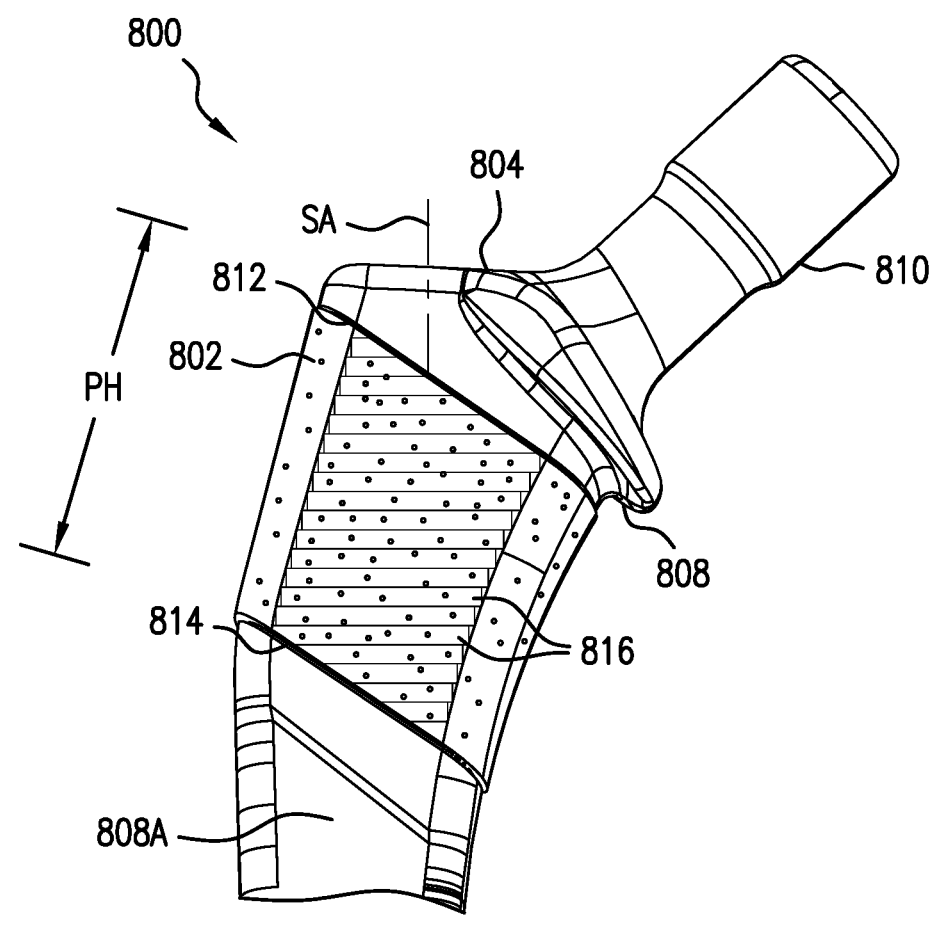
FIG. 23 is a front view of the femoral hip stem shown in FIG. 20 with yet a different groove pattern formed in the porous material.
Figure 24:
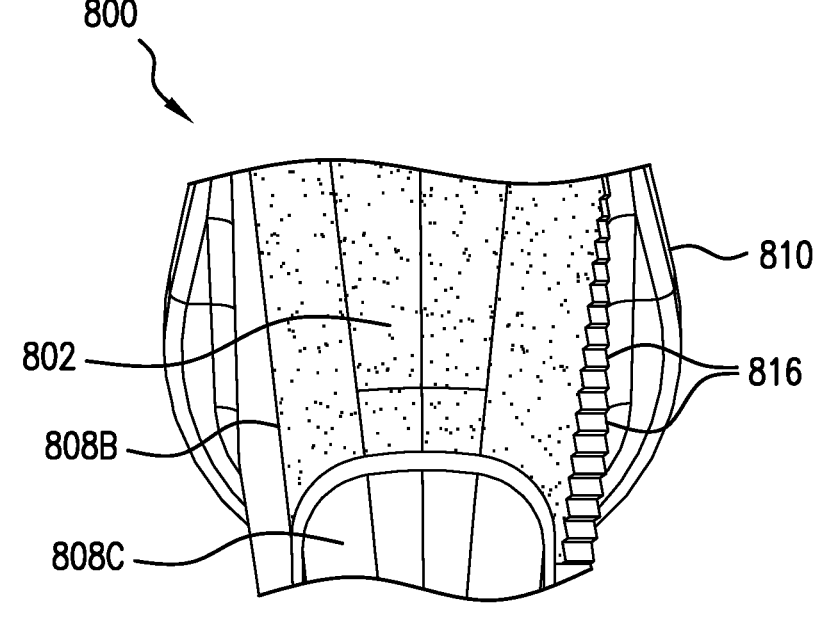
FIG. 24 is a side view of the femoral hip stem shown in FIG. 23.

Referring now to FIGS. 23-24, the orthopaedic implant shown in FIGS. 20-22 is shown with grooves 816 having a different orientation. The grooves 816 shown in FIGS. 23-24 are formed in the porous ingrowth material 802 on the anterior face 808A and oriented in a medial-lateral plane of the hip stem 804 to help prevent movement of the stem 804 in the proximal to distal direction. Other than the direction in which the grooves 816 extend, the grooves 816 shown in FIGS. 23-24 can be otherwise similar to the grooves 806 shown in FIGS. 20-22.

Figure 25:
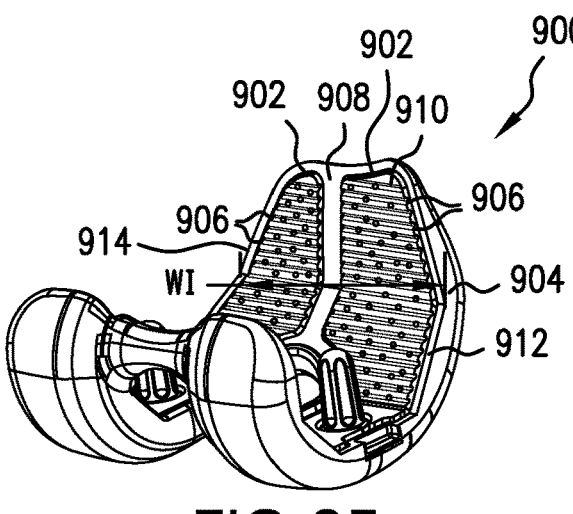
FIG. 25 is a perspective view of an embodiment of a femoral knee implant according to the present invention with a porous material having grooves formed therein.
Figure 26:
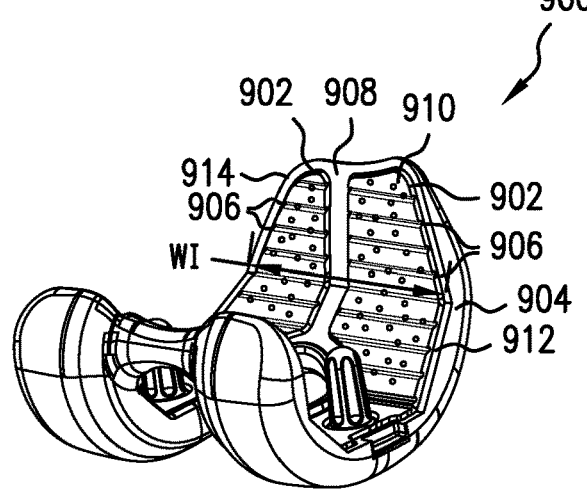
FIG. 26 is a perspective view of the femoral knee implant shown in FIG. 25 with a different groove pattern formed in the porous material.

Referring now to FIGS. 25-26, yet another embodiment of an orthopaedic implant 900 according to the present invention is shown which includes a porous ingrowth material 902 placed on a femoral knee implant 904 similar to previously described femoral knee implant 702. As can be seen, the porous ingrowth material 902 has grooves 906 formed therein and is placed on an interior surface 908 of a mounting portion 910 of the femoral knee implant 904. The formed grooves 906 span the medial to lateral regions of the implant 904, i.e., the grooves 906 extend in a medial-lateral direction. The medial-lateral grooves 906 can ease implantation of the implant 904 and prevent movement of the implant 904 after implantation. The grooves 906 may cover 0-100% of an implant width WI, and the grooves 906 may originate from a medial side 912 of the implant 904, a lateral side 914 of the implant 904, or any point in between. The location, pattern, orientation, and distance between the grooves 906 can vary, as can be seen by comparing FIG. 25 to FIG. 26. Likewise, the groove geometry can vary as previously described. The grooves 906 can be located 0.010" to 0.500" from each other. Further, the grooves 906 can have a depth D of 0.005" to 0.040", a width W of 0.005" to 0.080", a tip radius RT of 0.001" to 0.040", and a groove angle $\alpha$ of 0° to 120°. Further, the rake angle $\alpha R$ can range from −60° to +60°.

Figure 27:
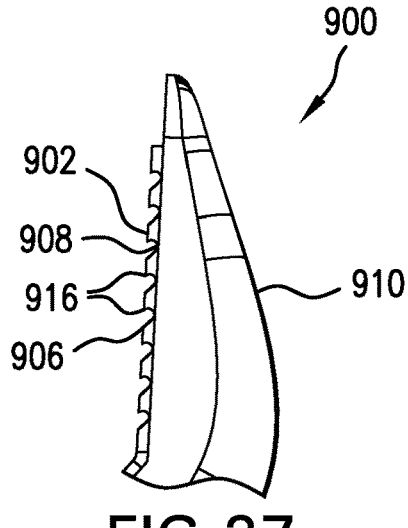
FIG. 27 is a side view of the femoral knee implant shown in FIG. 26.

Referring now to FIG. 27, a side view of the implant 900 shown in FIG. 26 is shown. As can be seen, the grooves 906 are formed in the porous ingrowth material 902 such that hooks 916 are formed in the porous ingrowth material 902 that can make insertion of the implant 900 easier while also making removal of the implant 900 after implantation more difficult.

Figure 28:
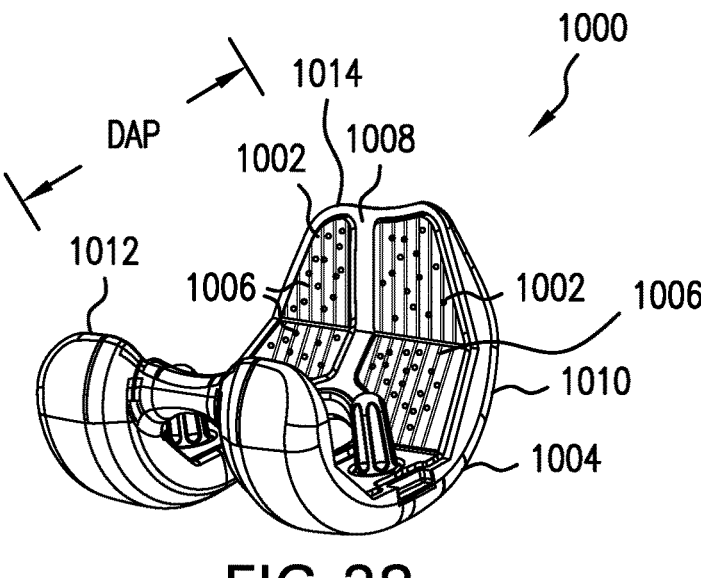
FIG. 28 is a perspective view of the femoral knee implant shown in FIG. 25 with yet another different groove pattern formed in the porous material.
Figure 29:
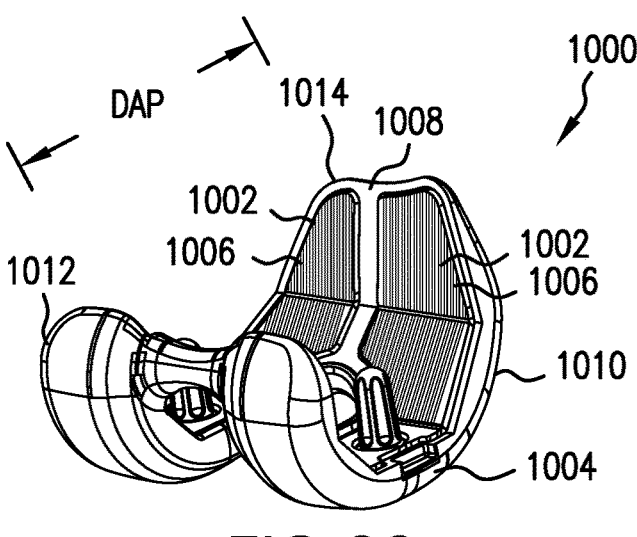
FIG. 29 is a perspective view of the femoral knee implant shown in FIG. 25 with yet another different groove pattern formed in the porous material.
Figure 30:
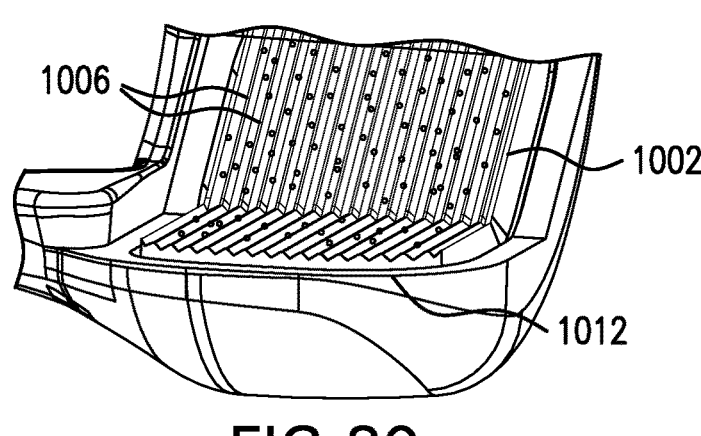
FIG. 30 is a close-up perspective view of the femoral knee implant shown in FIG. 29.

Referring now to FIGS. 28-30, yet another embodiment of an orthopaedic implant 1000 according to the present invention is shown having porous ingrowth material regions 1002 placed on a femoral knee implant 1004. The porous ingrowth material regions 1002 have grooves 1006 formed therein and can be placed on an interior surface 1008 of a mounting portion 1010 of the femoral knee implant 1004. The grooves 1006 span the anterior to posterior regions of the implant 1004, i.e., the grooves 1006 extend in an anterior-posterior direction. The anterior-posterior grooves 1006 can ease implantation of the implant 1004 and prevent movement of the implant 1004 in the medial-lateral directions after implantation. The grooves 1006 can cover 0-100% of an anterior to posterior distance DAP on the implant 1004, and the grooves 1006 can originate from an anterior side 1012 of the implant 1004, a posterior side 1014 of the implant 1004, or any point in between. The location, pattern, orientation, and distance between the grooves 1006 can vary, as can be seen by comparing FIG. 28 to FIG. 29. Likewise, the groove geometry can vary, as previously described. The grooves 1006 can be spaced to be to 0.500" from each other. Further, each groove can have a depth D of 0.005" to 0.040", a width W of 0.005" to 0.080", a tip radius RT of 0.001" to 0.040", and a groove angle $\alpha$ of 0° to 120°. Further, the rake angle $\alpha R$ can range from −60° to +60°.

Also provided by the present invention are devices and methods of attaching soft tissue or grafts to implants. The soft tissue can be any type of soft tissue including tendons, cartilage, muscle, etc. that might be encountered in a surgical setting. The present invention also provides devices and methods for attaching grafts that allow for soft tissue ingrowth to implants. The present invention can allow attachment of soft tissue or a graft to an implant with minimal damage to the tissue or graft, providing a way for a tendon to attach to a hip stem, minimizing damage caused by tendon ingrowth regions to the graft or tendon, and providing an instrument to aid in holding and tensioning a graft during surgery. It should be noted, in the context of the present invention, that "a graft" and "a soft tissue" can be used interchangeably, with reference to either also encompassing reference to the other.

Figure 31:
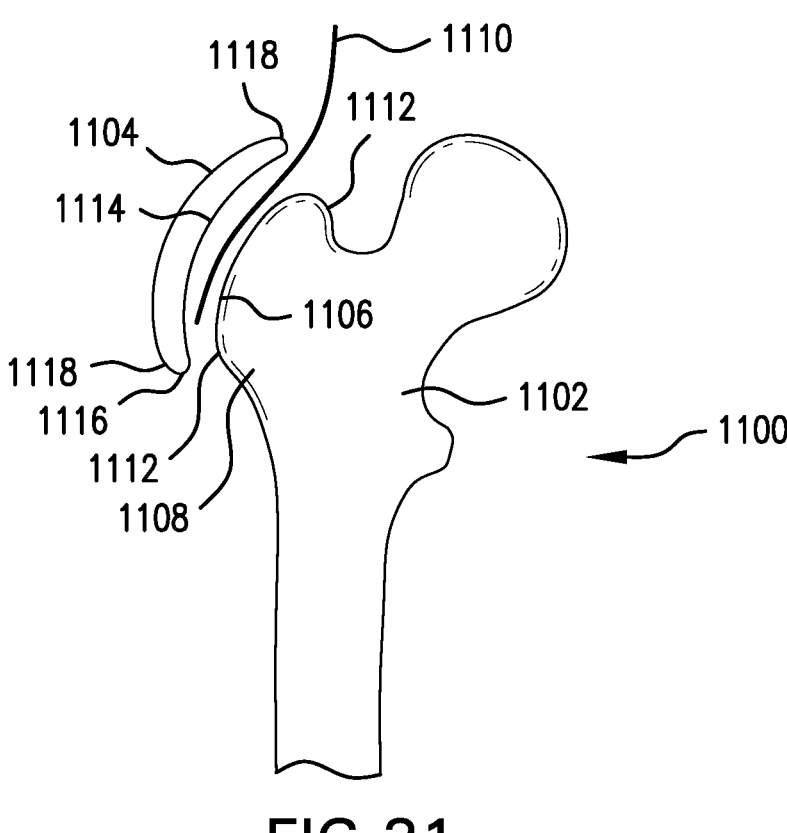
FIG. 31 is a perspective view of yet another embodiment of an orthopaedic implant according to the present invention having an adjustable holder.
Figure 32:
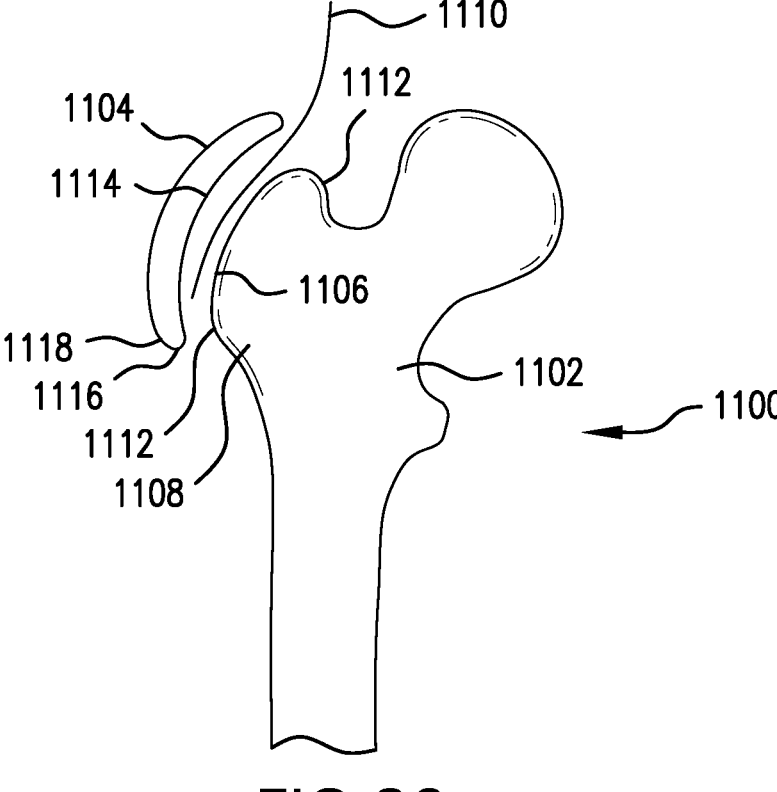
FIG. 32 is a perspective view of the orthopaedic implant shown in FIG. 31 with the adjustable holder tightened.

Referring now to FIGS. 31-32, another embodiment of an orthopaedic implant 1100 according to the present invention is shown. The orthopaedic implant 1100 includes an implant body 1102, shown as a femoral hip implant, and an adjustable holder 1104, shown as a cover plate, attached to the implant body 1102. As can be seen, the implant body 1102 defines an attachment region 1106 on an outer surface 1108 of the implant body 1102 where a graft 1110 can be attached to the implant body 1102. The attachment region 1106 can have rounded corners 1112 to produce low pressure on the graft 1110 when the graft 1110 is compressed to the attachment region 1106. The attachment region 1106 can be formed of the same material as the rest of the implant body 1102 or can be formed of a porous ingrowth material, such as those previously described, that is configured to allow the graft 1110 to integrate with the ingrowth material and form a strong attachment to the attachment region 1106. To compress the graft 1110 to the attachment region 1106, the holder 1104 has a compression surface 1114 facing the attachment region 1106. When the holder 1104 is moved from the position shown in FIG. 31 to the position shown in FIG. 32, the compression surface 1114 can force the graft 1110 against the attachment region 1106 and provide anchoring of the graft 1110 to the implant body 1102, either permanently or temporarily while the graft 1110 integrates with the attachment region 1106 to form a permanent attachment. To reduce the pressure exerted on the graft 1110 during compression, the holder 1104 can have an elongated curved shape and be tightened at a distal end 1116 of the holder 1104 such that the distal end 1116 of the holder 1104 is the area with the greatest compressive forces between the holder 1104 and the attachment region 1106. The holder 1104 can be overlengthened, relative to the graft 1110, such that no part of the graft 1110 is compressed between the distal end 1116 of the holder 1104 and the attachment region 1106, allowing the holder 1104 to be pressed tightly against the implant body 1102 without compressing the graft 1110 in the area of the highest compression forces. The curved shape of the holder 1104 can also have rounded corners 1118 that approximately match the curvature of the rounded corners 1112 of the attachment region 1106 but have a slight deviation of 1-5% of the curvature away from the distal end 1116 so there is a small clearance formed between the compression surface 1114 and the attachment region 1106 when the holder 1104 is fully tightened to the implant body 1102. Such a deviation in the curvature of the rounded corners 1118 of the compression surface 1114 away from the distal end 1116 can reduce the pressure exerted on the graft 1110 and decrease damage to the graft 1110 by decreasing the rapid change in stiffness between the portion of the graft 1110 that is compressed and the portion of the graft 1110 that is uncompressed.

Figure 33:
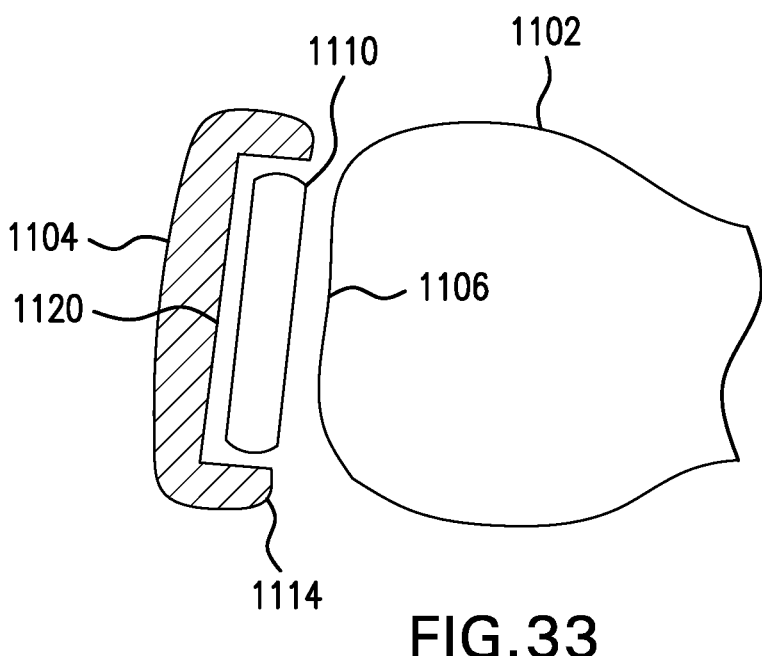
FIG. 33 is a top view of the orthopaedic implant shown in FIG. 31.

Referring now to FIG. 33, a top view of the orthopaedic implant 1100 shown in FIGS. 31-32 is shown. As can be seen, a channel 1120 can be formed in the holder 1104 where the graft 1110 will be located during compression. The channel 1120 allows for a reduced pressure across the length of the graft 1110 while still protecting the graft 1110 from outside contact and holding the graft 1110 to the attachment region 1106 of the implant body 1102.

Figure 34:
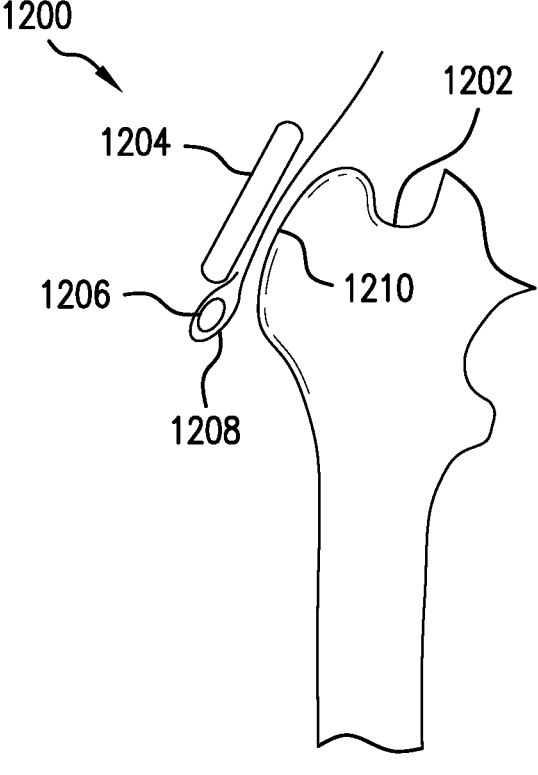
FIG. 34 is a perspective view of yet another embodiment of an orthopaedic implant according to the present invention having an adjustable holder with a roller.

Referring now to FIG. 34, another embodiment of an orthopaedic implant 1200 according to the present invention is shown that includes an implant body 1202, shown as a femoral hip stem, and an adjustable holder 1204 attached to the hip stem 1202. As can be seen, a roller 1206 can be attached to the holder 1204 that allows for a graft 1208 to be wrapped around the roller 1206. Wrapping the graft 1208 around the roller 1206 allows for a graft with an overly large length to be shortened and retained against an attachment region 1210 of the hip stem 1202. In such a configuration, the graft 1208 can be tied around the roller 1206 to keep the graft 1208 attached to the roller 1206 and then compressed between the holder 1204 and the attachment region 1210.

Figure 35:
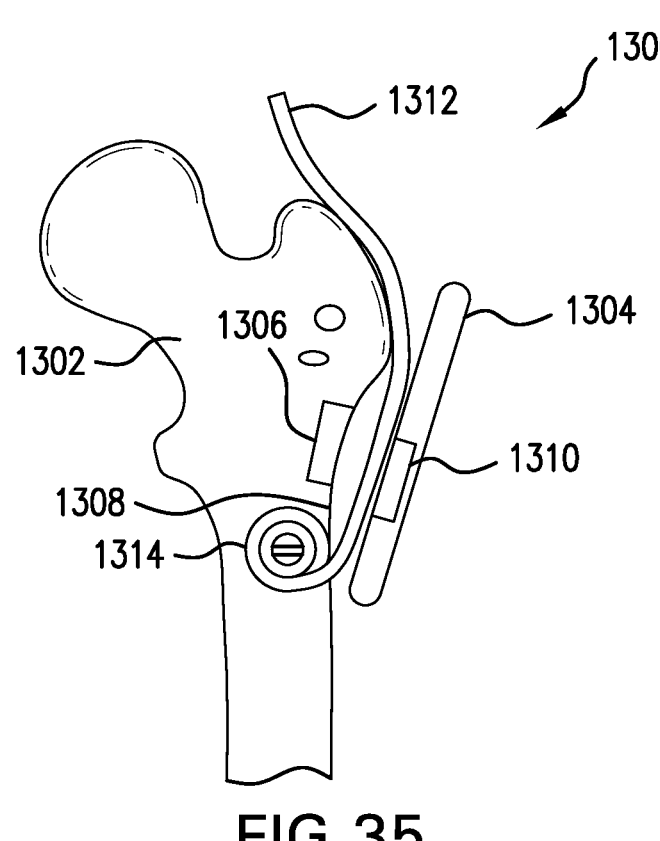
FIG. 35 is a perspective view of yet another embodiment of an orthopaedic implant according to the present invention having an adjustable holder with a ratcheting mechanism.

Referring now to FIG. 35, yet another embodiment of an orthopaedic implant 1300 according to the present invention is shown that includes an implant body 1302, shown as a femoral hip stem, and an adjustable holder 1304 attached to the hip stem 1302. The hip stem 1302 can have an ingrowth material 1306 attached to an attachment region 1308 of the hip stem 1302 and the holder 1304 can also have an ingrowth material 1310 that aligns with the ingrowth material 1306 of the hip stem 1302. A graft 1312 can be placed between the two ingrowth materials 1306 and 1310 and connected to a ratcheting mechanism 1314 attached to the hip stem 1302 by wrapping the graft 1312 around the ratcheting mechanism 1314. The ratcheting mechanism 1314 can then be turned to apply tension to the graft 1312 and tighten the graft 1312, holding the graft 1312 in place between the two ingrowth materials 1306 and 1310. Such a configuration allows the tension in the flexible graft 1312 to be conveniently adjustable during surgery.

Figure 36:
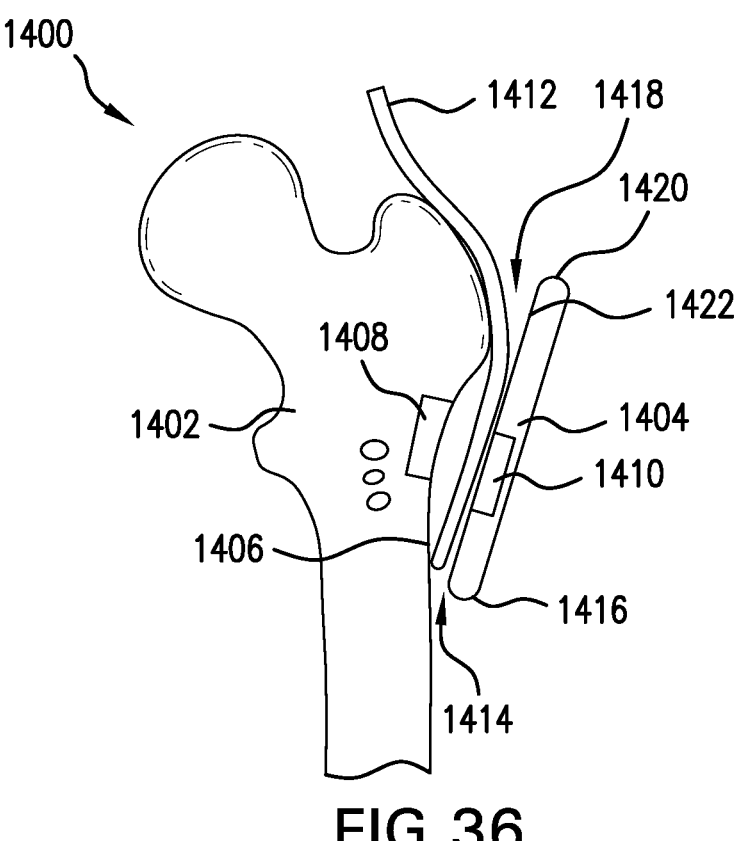
FIG. 36 is a perspective view of yet another embodiment of an orthopaedic implant according to the present invention having an adjustable holder with a compliant material placed on the holder.

Referring now to FIG. 36, yet another embodiment of an orthopaedic implant 1400 according to the present invention is shown that includes an implant body 1402, shown as a femoral hip stem, and a holder 1404 attached to the hip stem 1402. The implant body 1402 can have an attachment region 1406 with an ingrowth material 1408 and the holder 1404 can have a corresponding ingrowth material 1410 that is aligned with the ingrowth material 1408 of the attachment region 1406 so that when the holder 1404 is tightened against the hip stem 1402, the two ingrowth materials 1408 can both be contacting a graft 1412 held between the holder 1404 and hip stem 1402. The shape of the holder 1404 can be adjusted so that a pinch point 1414 is formed between the holder 1404 and the hip stem 1402 adjacent a distal end 1416 of the holder 1404 while a gap 1418 is formed between the holder 1404 and hip stem 1402 adjacent a proximal end 1420 of the holder 1404. The pinch point 1414 can be where the greatest compressive forces are applied to the graft 1412 by the holder 1404 and hip stem 1402, while the gap 1418 is where there are few, if any, compressive forces applied to the graft 1412 by the holder 1404 and hip stem 1402. To better hold the graft 1412 between the holder 1404 and hip stem 1402, a compliant material 1422 can be placed on the holder 1404 adjacent to the gap 1418 that will be deformed as the compliant material 1422 presses against the graft 1412 and hip stem 1402. The compliant material 1422 can thus be a relatively soft and compressible material such as additional graft material, polyurethane, polyethylene, etc. that provides additional coverage and fixation of the graft 1412 with little increase in the compressive forces applied to the graft 1412 adjacent to the gap 1418.

Figure 37:
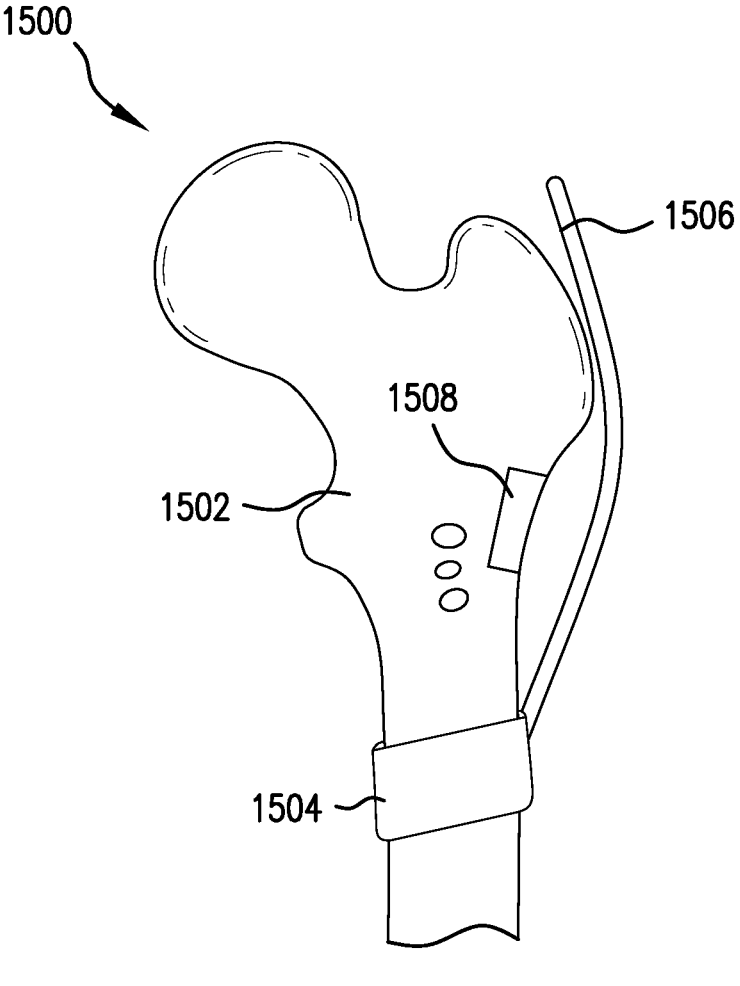
FIG. 37 is a perspective view of yet another embodiment of an orthopaedic implant according to the present invention having a holding collar and an ingrowth pad.

Referring now to FIG. 37, another embodiment of an orthopaedic implant 1500 according to the present invention is shown that includes an implant body 1502 and a collar 1504 affixed to the implant body 1502. The collar 1504 can be affixed to the implant body 1502 by a press fit, adhesive, or any other suitable way of affixing the collar 1504 to the implant body 1502 such that the collar 1504 is not easily removed from the implant body 1502. The collar 1504 can be formed of any biocompatible material and can also have an ingrowth material (not shown) in a region adjacent to where the collar 1504 is affixed to the implant body 1502. The collar 1504 can allow for a graft 1506, which can be formed of a synthetic or natural material, to be fixed to the collar 1504 to affix the graft 1506 to the implant body 1502. The graft 1506 can be held between the collar 1504 and the implant body 1502, if compression is desired, or attached to the collar 1504 without compressing the graft 1506 between the collar 1504 and the implant body 1502. Optionally, an ingrowth pad 1508 formed of an ingrowth material can be connected to the implant body 1502 and the graft 1506 held against the ingrowth pad 1508 to allow the graft 1506 to infiltrate the ingrowth pad 1508 and form another attachment point to the implant body 1502.

Figure 38A:
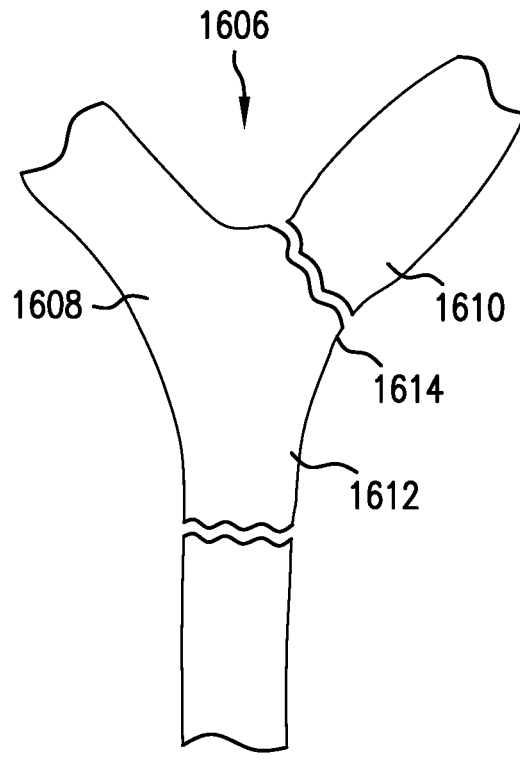
FIG. 38A illustrates a bifurcated graft.
Figure 38B:
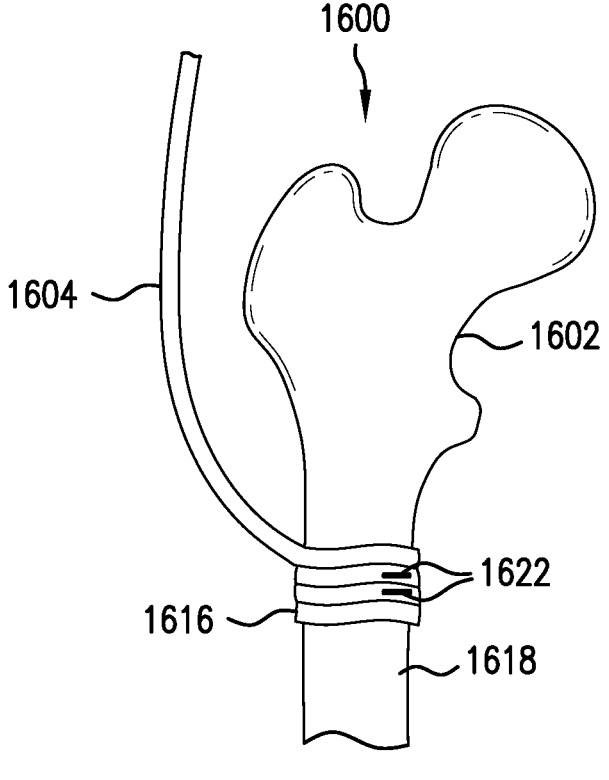
FIG. 38B is a perspective view of the bifurcated graft shown in FIG. 38A being used as a collar wrapped around a hip stem.

Referring now to FIGS. 38A-38B, another embodiment of an orthopaedic implant 1600 is shown that includes an implant body 1602 and a collared graft 1604 attached to the implant body 1602. The collared graft 1604 can be formed from a bifurcated graft 1606, shown in FIG. 38A, which has a first branch 1608 and a second branch 1610 connected to a main body 1612 of the bifurcated graft 1606. The bifurcated graft 1606 can be, for example, a tendon or cartilage that is naturally bifurcated and taken from the body or a synthetic material shaped to include a bifurcation. To form the collared graft 1604 from the bifurcated graft 1606, a portion of the second branch 1610 can be removed to form a collar region 1614 in the bifurcated graft 1606, with a portion of the main body 1612 being connected to the collar region 1614 to form a collar 1616 of the collared graft 1604, which is seen in FIG. 38B. The collar 1616 can be formed prior to sliding over a stem 1618 of the implant body 1602 or formed by looping the portion of the main body 1612 around the stem 1618 and then connecting the portion to the collar region 1614 to form the collar 1616, which will be looped around the stem 1618. If desired, sutures 1622 can be used to reduce slippage between the collared graft 1604 and the implant body 1602.

Figure 39:
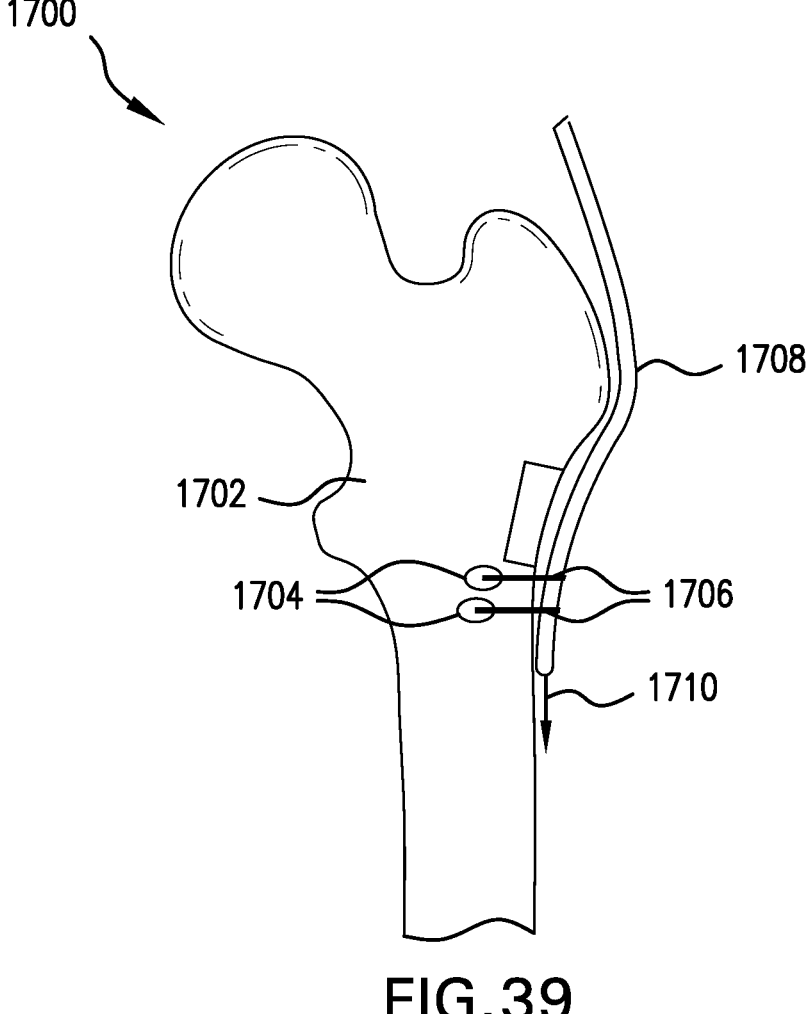
FIG. 39 is a perspective view of yet another embodiment of an orthopaedic implant according to the present invention with sutures holding a graft to an ingrowth pad of the orthopaedic implant.

Referring now to FIG. 39, another embodiment of an orthopaedic implant 1700 according to the present invention is shown that includes an implant body 1702 having a series of openings 1704 formed therein and sutures 1706 looped through the openings 1704 to press a graft 1708 against the implant body 1702. Prior to looping the sutures 1706 through the openings 1704, the graft 1708 can be pulled in a tensioning direction, signified by arrow 1710, by an instrument (not shown) to keep the graft 1708 taut prior to being affixed to the implant body 1702 by the sutures 1706. While two suture loops 1706 and corresponding openings 1704 are shown, the number of openings 1704 can be varied, as desired, to be as few as one or more than two. It is also contemplated that the sutures 1706 can be replaced by surgical staples.

Figure 40A:
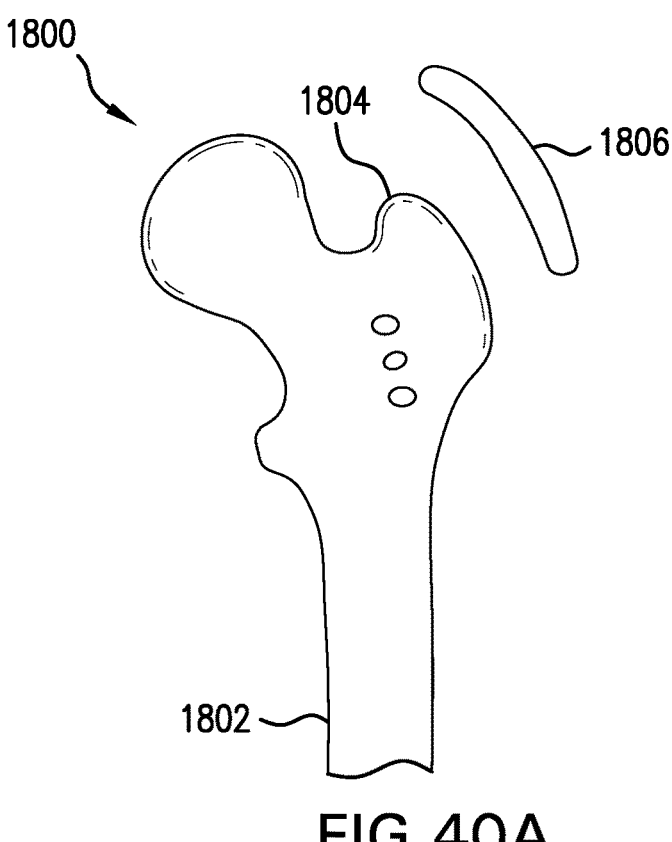
FIG. 40A is a perspective view of yet another embodiment of an orthopaedic implant according to the present invention with a short greater trochanter that cannot reach a tendon.
Figure 40B:
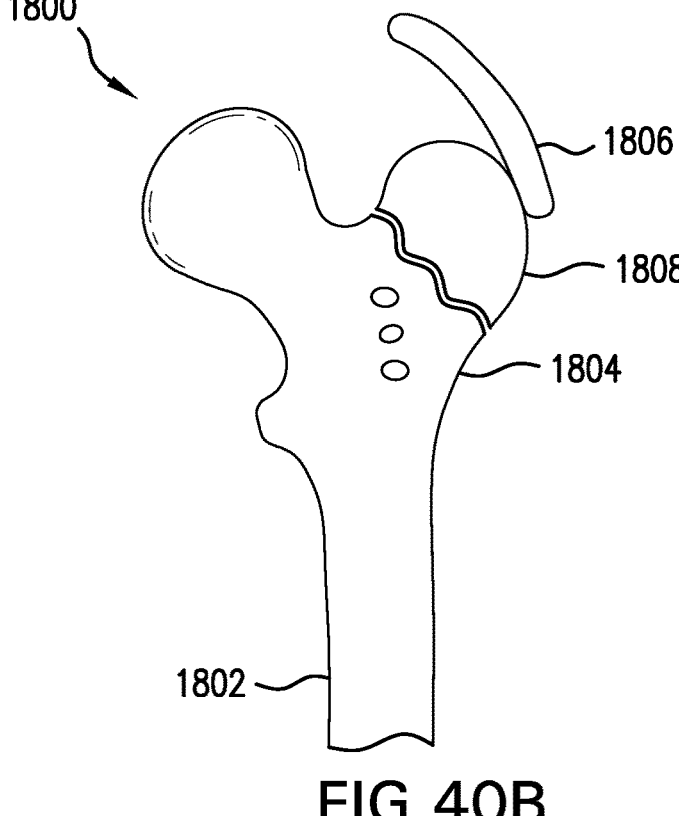
FIG. 40B is a perspective view of the orthopaedic implant shown in FIG. 40A with an elongated greater trochanter that can reach the tendon shown in FIG. 40A.

Referring now to FIGS. 40A and 40B, yet another embodiment of an orthopaedic implant 1800 according to the present invention is shown that includes an implant body 1802 with a greater trochanter 1804. As can be seen in FIG. 40A, after implantation it can be discovered that the greater trochanter 1804 of the implant body 1802 does not have sufficient length to reach a tendon 1806 that is to be attached to the greater trochanter 1804. Further stretching the tendon 1806 may cause the tendon 1806 to snap or be excessively strained, and thus is not a viable option. To allow for the tendon 1806 to be attached to the greater trochanter 1804, and referring specifically to FIG. 40B, an extension 1808 can be attached to the greater trochanter 1804 that effectively lengthens the greater trochanter 1804 and allows for the tendon 1806 to be attached to the implant body 1802. The extension 1808 can be formed from the same material as the greater trochanter 1804, to give similar attachment characteristics, or be a different material. The extension 1808 can also include any of the herein described features to allow the tendon 1806 to be attached to the extension 1808. Further, the extension 1808 can be more flexible than the greater trochanter 1804 to decrease the gradient in stiffness between the tendon 1804 and the greater trochanter 1804.

Figure 41:
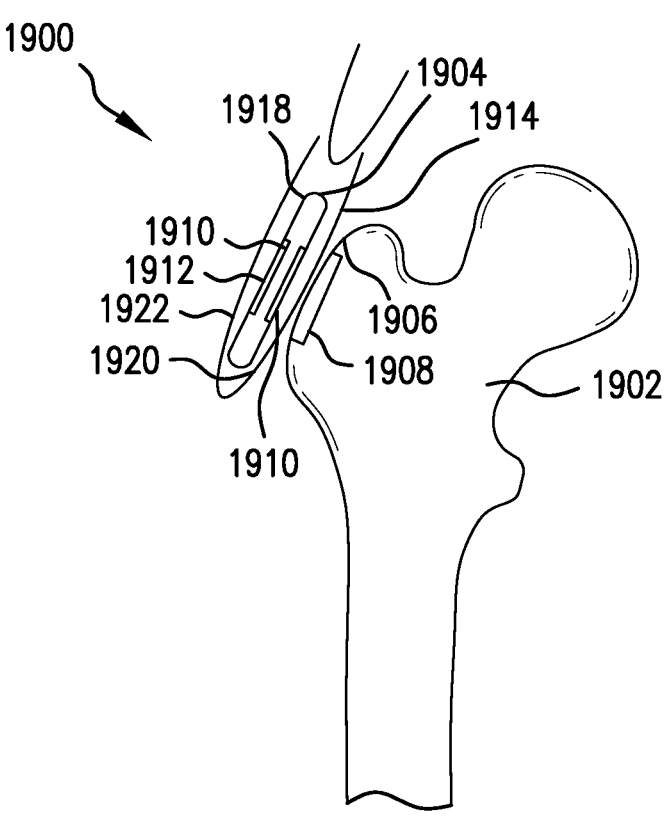
FIG. 41 is a perspective view of yet another embodiment of an orthopaedic implant according to the present invention with an adjustable holder holding a graft between two ingrowth pads.

Referring now to FIG. 41, yet another embodiment of an orthopaedic implant 1900 according the present invention is shown that includes an implant body 1902 and a holder 1904 connected to the implant body 1902. The implant body 1902 has an attachment region 1906, similar to previously described implant bodies, and an ingrowth material 1908, shown as an ingrowth pad, in the attachment region 1906. The holder 1904 also has a pair of ingrowth materials 1910, shown as pads, on opposite surfaces of the holder 1904 to contact interior surfaces 1912 of a graft 1914 attached to a tendon 1916. The graft 1914 has an opening 1918 formed therein to partially split the graft 1914 into an interior portion 1920 that will be held between the holder 1904 and the attachment region 1906 and an exterior portion 1922 that will be on the exterior of the holder 1904. The interior portion 1920 can thus contact multiple ingrowth pads 1908, 1910 and be compressed between the holder 1904 and the attachment region 1906 while the exterior portion 1922 also contacts an ingrowth pad 1910. Such a configuration increases the amount of surface area of the graft 1914 that is in contact with ingrowth material and can hasten the attachment of the graft 1914 to the orthopaedic implant 1900.

Figure 42:
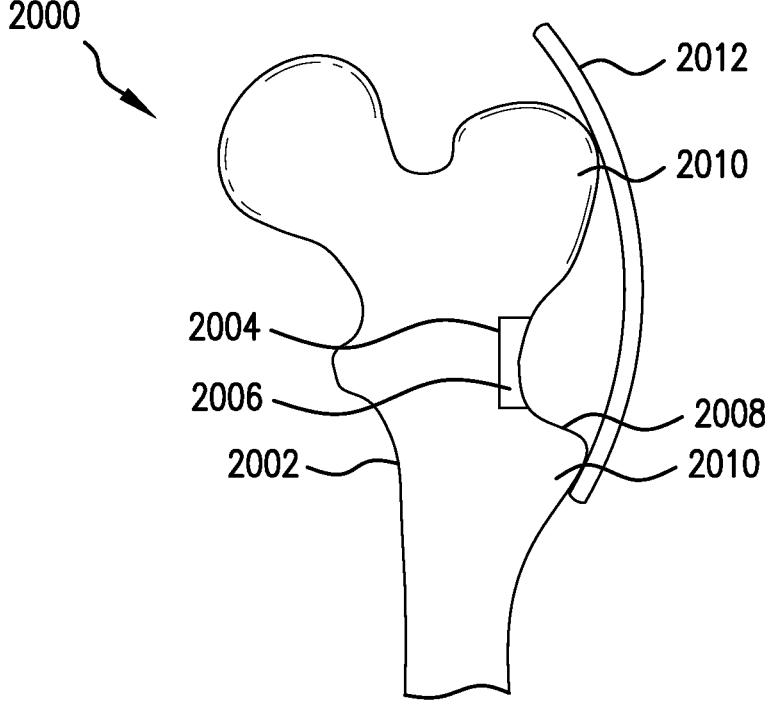
FIG. 42 is a perspective view of yet another embodiment of an orthopaedic implant according to the present invention having a recessed ingrowth material.

When ingrowth regions are attached to a surface of an implant, it is possible that the ingrowth regions will damage the attached graft due the ingrowth regions being raised relative to the surface. To reduce the risk of damage to an attached graft, and referring now to FIG. 42, an orthopaedic implant 2000 according to the present invention can have an implant body 2002 with a recess 2004 formed therein that is filled with a porous ingrowth material 2006 so the porous ingrowth material 2006 is flush with an outer surface 2008 of the implant body 2002. The implant body 2002 can also have protruding regions 2010 that are rounded with a large radius leading into the area with the recess 2004 and porous ingrowth material 2006 to prevent large stress concentrations on a graft 2012 that is held against the porous ingrowth material 2006. By having the ingrowth material 2006, which can be a porous ingrowth pad, in the recess 2004 and flush with the outer surface 2008, the risk that the graft 2012 will abrade against corners of the ingrowth pad 2006 and be damaged is reduced. It should be appreciated that while the gap between the graft 2012 and the porous ingrowth pad 2006 has been exaggerated in FIG. 42 to show better detail, the graft 2012 will normally be in contact or close to contacting the porous ingrowth pad 2006 after implantation.

Figure 43:
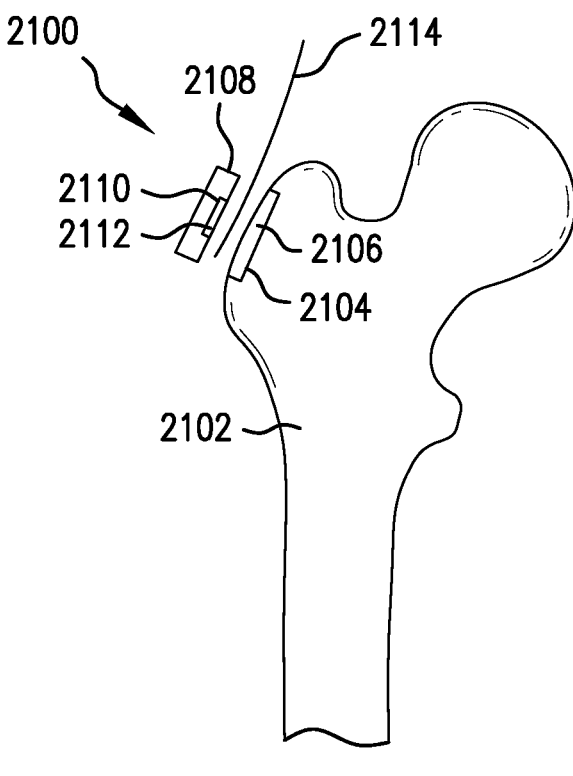
FIG. 43 is a perspective view of yet another embodiment of an orthopaedic implant according to the present invention with an adjustable holder holding a graft between two ingrowth pads.

Referring now to FIG. 43, yet another embodiment of an orthopaedic implant 2100 according to the present invention is shown that includes an implant body 2102 with a recess 2104 formed therein and a porous ingrowth material 2106 placed in the recess 2104. A holder 2108 can be connected to the implant body 2102 and also have a recess 2110 formed therein with a porous ingrowth material 2112 placed in the recess 2110. A graft 2114 can be compressed between the holder 2108 and implant body 2102 so that the graft 2114 contacts both porous ingrowth materials 2106 and 2112, which can lead to increased integration of the graft 2114 with the implant 2100 and reduced risk of wear due to abrasion with the porous ingrowth materials 2106 and 2112.

Figure 44:
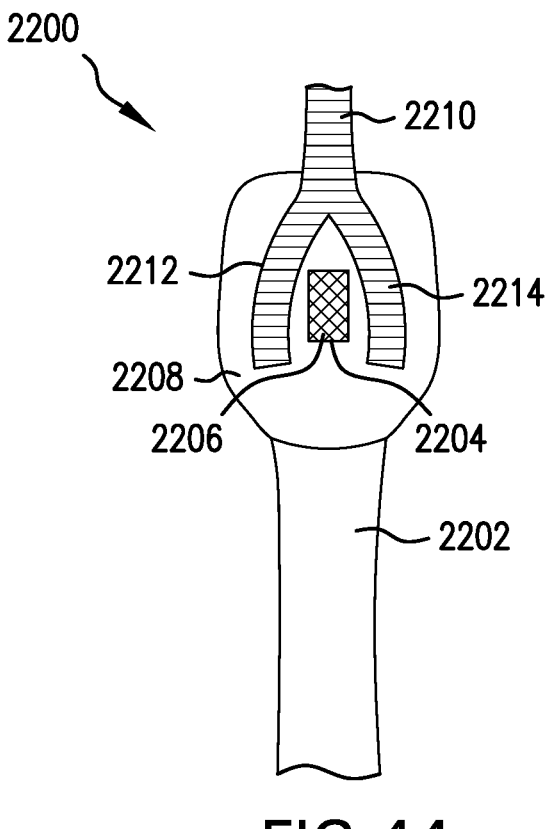
FIG. 44 is a lateral view of the orthopaedic implant shown in FIG. 43 with the holder removed and a bifurcated graft placed around an ingrowth pad.

Referring now to FIG. 44, yet another embodiment of an orthopaedic implant 2200 according to the present invention is shown that includes an implant body 2202 with a recess 2204 formed therein and a porous ingrowth material 2206 placed in the recess 2204. The recess 2204 can be formed, for example, in a greater trochanter 2208 of the implant body 2202 and the porous ingrowth material 2206 can be a porous ingrowth pad placed in the recess 2204. The orthopaedic implant 2200 can further include a holder, such as a plate, which is not shown to illustrate how a bifurcated graft 2210 with a first branch 2212 and a second branch 2214 can be held between the implant body 2202 and plate with the first branch 2212 and second branch 2214 placed on opposite sides of the porous ingrowth pad 2206. The porous ingrowth pad 2206, therefore, can be placed between the first branch 2212 and second branch 2214 to allow ingrowth of both branches 2212 and 2214 to the porous ingrowth pad 2206.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic implant, comprising:
   an implant body comprising a biocompatible material and configured to be implanted at an anatomical location, the implant body defining an attachment region on an outer surface of the implant body;
   an adjustable holder attached to the implant body and having a compression surface facing the attachment region, the adjustable holder being configured to be implanted at the anatomical location with the implant body and adjustably compress a soft tissue and/or a graft material between the compression surface and the attachment region; and
   a ratcheting mechanism attached to the implant body and configured to apply tension to the soft tissue and/or the graft material connected to the ratcheting mechanism.

2. The orthopaedic implant of claim 1, further comprising at least one ingrowth material attached to the attachment region.

3. The orthopaedic implant of claim 2, wherein the at least one ingrowth material comprises a plurality of ingrowth materials.

4. The orthopaedic implant of claim 1, wherein the adjustable holder comprises a cover attached to the implant body.

5. The orthopaedic implant of claim 1, wherein the adjustable holder has a channel formed therein.

6. The orthopaedic implant of claim 1, further comprising a compliant material attached to the adjustable holder.

7. The orthopaedic implant of claim 6, wherein the implant body and the adjustable holder define a gap therebetween adjacent a proximal end of the adjustable holder, the compliant material being attached to the adjustable holder adjacent to the gap.

8. The orthopaedic implant of claim 1, wherein the adjustable holder is at least one suture.

9. The orthopaedic implant of claim 1, wherein the adjustable holder has a recess formed therein and a porous ingrowth material placed in the recess.

10. The orthopaedic implant of claim 1, wherein the adjustable holder is a collar.

11. The orthopaedic implant of claim 10, wherein the collar comprises at least one of a tendon, cartilage, or a synthetic material.

12. The orthopaedic implant of claim 1, wherein the adjustable holder comprises a pair of ingrowth surfaces on opposite surfaces of the adjustable holder.

13. The orthopaedic implant of claim 1, further comprising a soft tissue and/or a graft material compressed between the adjustable holder and the attachment region and wrapped around the ratcheting mechanism.

14. The orthopaedic implant of claim 13, wherein turning of the ratcheting mechanism adjusts tension in the soft tissue and/or the graft material wrapped around the ratcheting mechanism.

15. A method of affixing a soft tissue and/or a graft material to an orthopaedic implant, the method comprising:

implanting the orthopaedic implant at an anatomical location, the orthopaedic implant comprising:

an implant body comprising a biocompatible material and defining an attachment region on an outer surface of the implant body;

an adjustable holder attached to the implant body and having a compression surface facing the attachment region; and a ratcheting mechanism attached to the implant body;

compressing the soft tissue and/or the graft material between the compression surface of the adjustable holder and the attachment region of the implant body; and wrapping the soft tissue and/or the graft material around the ratcheting mechanism.

16. The method of claim 15, further comprising adjusting the compression exerted on the soft tissue and/or the graft material by adjusting the position of the adjustable holder relative to the attachment region.

17. The method of claim 15, further comprising adjusting a tension in the soft tissue and/or the graft material by turning the ratcheting mechanism.

18. The method of claim 15, further comprising contacting at least one ingrowth material with soft tissue and/or the graft material.

* * * * *